(12) United States Patent
Soon-Shiong et al.

(10) Patent No.: US 12,403,178 B2
(45) Date of Patent: *Sep. 2, 2025

(54) USE OF CD33CAR MODIFIED HIGH AFFINITY NK CELLS (T-HANK) TO REDUCE MYELOID-DERIVED SUPPRESSOR CELLS SUPPRESSOR ACTIVITY (OR REDUCE NEGATIVE IMPACT ON NK CELL ACTIVITY)

(71) Applicant: ImmunityBio, Inc., Culver City, CA (US)

(72) Inventors: Patrick Soon-Shiong, Culver City, CA (US); Hans G Klingemann, Culver City, CA (US); Laurent H Boissel, Culver City, CA (US); Himani Chinnapen, Culver City, CA (US); Abhijit Dandapat, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 173 days.

This patent is subject to a terminal disclaimer.

(21) Appl. No.: 18/463,907

(22) Filed: Sep. 8, 2023

(65) Prior Publication Data
US 2024/0016849 A1    Jan. 18, 2024

Related U.S. Application Data

(63) Continuation of application No. 16/966,868, filed as application No. PCT/US2019/021647 on Mar. 11, 2019, now Pat. No. 11,813,292.

(60) Provisional application No. 62/641,915, filed on Mar. 12, 2018.

(51) Int. Cl.
| A61K 35/17 | (2015.01) |
| A61K 38/17 | (2006.01) |
| A61K 39/00 | (2006.01) |

(52) U.S. Cl.
CPC ...... *A61K 38/1774* (2013.01); *A61K 39/4613* (2023.05); *A61K 39/4631* (2023.05); *A61K 39/4644* (2023.05); *A61K 39/464411* (2023.05); *A61K 2239/48* (2023.05)

(58) Field of Classification Search
CPC .......................... A61K 35/17; A61K 38/1774
See application file for complete search history.

(56) References Cited

U.S. PATENT DOCUMENTS

| 7,098,008 B2 | 8/2006 | Park et al. |
| 7,618,817 B2 | 11/2009 | Campbell |
| 8,034,332 B2 | 10/2011 | Klingemann |
| 8,313,943 B2 | 11/2012 | Campbell |
| 9,150,636 B2 | 10/2015 | Campbell |
| 9,181,322 B2 | 11/2015 | Campbell |
| 10,138,462 B2 | 11/2018 | Klingemann |
| 2002/0068044 A1 | 6/2002 | Klingemann |
| 2013/0189268 A1 | 7/2013 | Du et al. |
| 2013/0280285 A1 | 10/2013 | Schonfeld et al. |
| 2014/0242701 A1 | 8/2014 | Shiku et al. |
| 2014/0274909 A1 | 9/2014 | Orentas et al. |

FOREIGN PATENT DOCUMENTS

| CA | 3 091 224 A1 | 9/2019 |
| CN | 112004829 A | 11/2020 |
| WO | 98/49268 A1 | 11/1998 |
| WO | 99/24566 A1 | 5/1999 |
| WO | 00/20460 A1 | 4/2000 |
| WO | 2014/039523 A1 | 3/2014 |
| WO | 2014/099671 A1 | 6/2014 |
| WO | 2015075470 A1 | 5/2015 |
| WO | 2016014576 A1 | 1/2016 |
| WO | 2016201304 A1 | 12/2016 |
| WO | 2017214333 A1 | 12/2017 |
| WO | 2019018382 A1 | 1/2019 |
| WO | 2019/177986 A1 | 9/2019 |

OTHER PUBLICATIONS

Office Action received for Canadian Patent Application Serial No. 3,091,224 dated Jul. 26, 2022, 4 pages.
Rafiq et al., "NK-92 Cells Engineered with Anti-CD33 Chimeric Antigen Receptors (CAR) for the Treatment of Acute Myeloid Leukemia (AML)" Jun. 2015, Cytotherapy, vol. 17, p. S23.
Office Action received for Canadian Patent Application Serial No. 3091224 dated Aug. 16, 2021, 5 pages.
Eksioglu et al., "Novel Therapeutic Approach to Improve Hemtopoiesis in low risk MDS by Targeting MDSCs with the Fc-engineered CD33 Antibody BI 836858", Leukemia, Oct. 2017; 31 (10): 2172-2180.
International Search Report with International Application No. PCT/US2019/021647 filing date: Mar. 11, 2019, p. 1-7.
Mougiakakos et al., "CD33/CD3-Bispecific T-Cell Engaging (BiTE®) Antibody Constructs Eficiently Target Monocytic CD14+ hla-DRlow IDO+ aml-MDSCs" Dec. 7, 2017, Abstract, p. 1-6.

(Continued)

*Primary Examiner* — Tracy Vivlemore
*Assistant Examiner* — Eric J Rogers
(74) *Attorney, Agent, or Firm* — Umberg Zipser LLP

(57) ABSTRACT

The present application is directed to methods and compositions that are useful for reducing the number of myeloid-derived suppressor cells (MDSC), tumor associated macrophages (TAM), or both in a subject. The methods include administering an antigen binding protein that binds to an antigen expressed by MDSC and/or TAM, or administering a modified T cell or NK-92 cell that expresses an antigen binding protein that binds to an antigen expressed by MDSC and/or TAM, or a combination of both, to a subject. For example, the antigen binding protein can bind to CD33 expressed by MDSC and/or TAM. The methods and compositions are useful for treating a disease associated with MDSC and/or TAM infiltration into a tissue or tumor.

22 Claims, 11 Drawing Sheets

Specification includes a Sequence Listing.

(56) References Cited

OTHER PUBLICATIONS

O'Hear et al., "Anti-CD33 chimeric antigen receptor targeting of acute myeloid leukemia" Haematologica, 2014, pp. 1-9.

Bronte et al., "Recommendations for myeloid-derived suppressor cell nomenclature and characterization standards", Nature, 2016, vol. 7, No. 12150, pp. 1-10 (cited from specification).

Herberman et al., "Natural killer cells: their roles in defenses against disease", Science, 1981, vol. 214, pp. 24-30 (cited from specification).

Haynes, et al., "Redirecting Mouse CTL Against Colon Carcinoma: Superior Signaling Efficacy of Single-Chain Variable Domain ChimerasContaining TCR-ζ vs FcεRI-γ", Journal of Immunology, 2001, vol. 166, pp. 182-187 (cited from specification).

Cartellieri et al., "Chimeric Antigen Receptor-Engineered T Cells for Immunotherapy of Cancer", Journal of Biomedicine and Biotechnology, 2010, vol. 2010, No. 956304, 14 pages (cited from specification).

Hermanson et al., "Utilizing chimeric antigen receptors to direct natural killer cell activity", Frontiers in Immunology, 2015, vol. 6, No. 195, 6 pages (cited from specification).

Smith et al., "Comparison of Biosequences", Advances in applied Mathematics, 1981, vol. 2, pp. 482-489 (cited in specification).

Needleman et al., "A general method applicable to the search for similarities in the amino acid sequence of two proteins", Journal of Molecular Biology, 1970, vol. 48, pp. 443-453 (cited in specification).

Pearson et al., "Improved tools for biological sequence comparison", Proceedings of the National of Sciences of The United States of America, 1988, vol. 85, No. 8, pp. 2444-2448 (cited in specification).

Altschul et al., "Basic Local Alignment Search Tool", Journal of Molecular Biology, 1990, vol. 215, No. 3, pp. 403-410 (cited from specification).

Henikoff et al., "Amino acid substitution matrices from protein blocks", Proceedings of the National Academy of Science USA, 1992, vol. 89, No. 22, pp. 10915-10919 (cited from specification).

Yazawa et al., "Current Progress in Suicide Gene Therapy for Cancer", World Journal of Surgery, 2002, vol. 26, No. 7, pp. 783-789 (cited from specification).

Gong et al., "Characterization of a human cell line (NK-92) with phenotypical and functional characteristics of activated natural killer cells", Leukemia, 1994, vol. 8, No. 4 pp. 652-658 (cited from specification).

Kumar et al., "The Nature of Myeloid-Derived Suppressor Cells in the Tumor Microenvironment" Trends Immunology, 2016, 13 pages (cited specification).

Genard et al., "Reprogramming of Tumor-Associated Macrophages with Anticancer Therapies: Radiotherapy versus Chemo- and immunotherapies", Frontiers in Immunology, 2017, vol. 8, No. 828, 19 pages (cited from specification).

Konstantinidis et al., "Targeting IL-2 to the endoplasmic reticulum confines autocrine growth stimulation to NK-15 92 cells", Experimental Hematology, 2005, vol. 33, No. 2, pp. 159-164.

Garcia-Sanchez et al., "Cytosine deaminase adenoviral vector and 5-fluorocytosine selectively reduce breast cancer cells 1 million-fold when they Contaminate Hematopoietic Cells: A Potential Purging Method for Autologous Transplantation", Blood, 1998, vol. 92, No. 2, pp. 672-682 (cited from specification).

Touati et al., "A suicide gene therapy combining the improvement of cyclophosphamide tumor cytotoxicity and the development of an anti-tumor immune response.", Current Gene Therapy, 2014, vol. 14, pp. 236-246 (cited from specification).

Stasi et al., "Inducible apoptosis as a safety switch for adoptive cell therapy", New England Journal of Medicine, 2011, vol. 365, 17 pages (cited from specification).

Morgan A Richard, "Live and Let Die: A New Suicide Gene Therapy Moves to the Clinic", Molecular Therapy, 2012, vol. 20, No. 1, pp. 11-13 (cited from specification).

International Preliminary Report on Patentability Chapter I received for PCT Application Serial No. PCT/US2019/021647 dated Sep. 24, 2020, 10 pages.

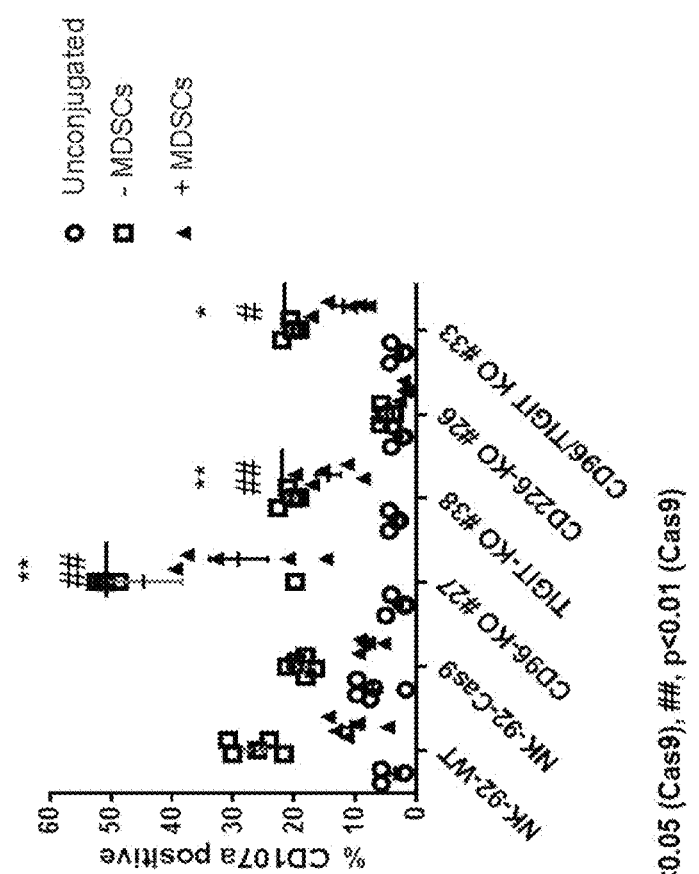
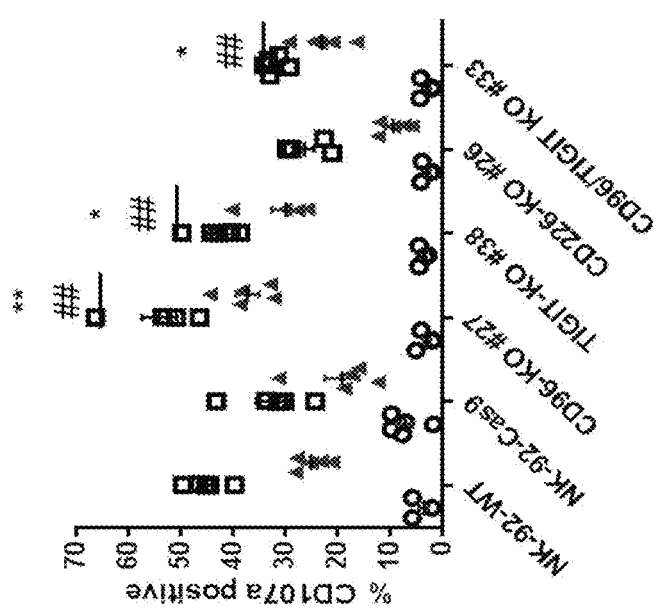
FIG. 4

Codon-optimized CD33ScfV-P2A-CD16-IRES-ERIL2 sequence

ATGGACTGGATCTGGCGCATCCTCTTCCTCGTCGGCGCTGCTACCGGCGCTCATTCGGCCCAGCCGGCCGACATTCAAATG
ACTCAGTCCCCTTCCAGCTTGTCAGCCTCAGTAGGGGACCGGGTCACGATCACCTGTCGAGCGTCTGAGTCAGTGGATAAC
TACGGGATTTCTTTCATGAACTGGTTCCAGCAGAAGCCCGGCAAAGCTCCTAAGCTCCTTATATATGCAGCCTCAAATCAG
GGGAGCGGTGTTCCTAGTCGCTTCAGTGGAAGCGGTAGCGGTACGGACTTTACGTTGACGATAAGTAGCCTTCAGCCAGAT
GACTTTGCCACTTATTATTGTCAGCAGTCTAAGGAAGTTCCTTGGACGTTTGGCCAAGGAACGAAGGTCGAAATCAAAGGG
GGAGGGGGCTCAGGAGGGGGCGGCAGTGGTGGTGGAGGCTCTCAAGTCCAACTCGTACAGTCTGGCGCGGAGGTTAAAAAG
CCGGGAAGCTCCGTGAAAGTATCCTGTAAGGCAAGCGGATACACCTTTACCGATTATAACATGCACTGGGTTAGGCAGGCG
CCCGGCCAAGGTCTGGAATGGATCGGTTATATTTATCCATACAACGGTGGTACCGGCTATAATCAGAAGTTTAAGAGTAAG
GCTACTATTACAGCGGATGAGTCAACCAATACTGCATACATGGAGCTCTCCTCACTCAGGAGCGAAGATACCGCAGTGTAT
TACTGTGCCCGAGGGAGACCAGCCATGGACTACTGGGGTCAGGGTACCCTTGTGACAGTATCTAGCGCGGCCGCGCTGAGC
AACAGCATCATGTACTTCAGCCACTTCGTGCCTGTGTTCCTGCCTGCCAAGCCTACAACAACACCAGCCCCTAGACCTCCA
ACCCCTGCCCCTACAATTGCCTCTCAGCCTCTGTCTCTGAGGCCCGAAGCTTGTAGACCTGCTGCTGGCGGAGCTGTGCAC
ACCAGAGGACTGGATTTCGCCTGCTTTTGGGTGCTGGTGGTCGTGGGCGGAGTGCTGGCTTGTTATTCTCTGCTGGTCACC
GTGGCCTTCATCATCTTTTGGGTCCGACTGAAGATCCAGGTCCGAAAGGCCGCCATCACCAGCTACGAGAAGTCTGATGGC
GTGTACACCGGCCTGAGCACCAGAAACCAGGAAACCTACGAGACACTGAAGCACGAAGCCCCCCAGGGATCCGGAGCT
ACTAACTTCAGCCTGCTGAAGCAGGCTGGAGACGTGGAGGAGAACCCTGGACCTATGGTGGCAGCTGCTGCTGCCTACAGCT
CTCCTGCTGCTGGTGTCCGCCGGCATGAGAACCGAGGATCTGCCTAAGGCCGTGGTGTTCCTGGAACCCCAGTGGTACAGA
GTGCTGGAAAAGGACAGCGTGACCCTGAAGTGCCAGGGCGCCTACAGCCCCGAGGACAATAGCACCCAGTGGTTCCACAAC
GAGAGCCTGATCAGCAGCCAGGCCAGCAGCTACTTCATCGACGCCGCCACCGTGGACGACAGCGGCGAGTATAGATGCCAG
ACCAACCTGAGCACCCTGAGCGACCCCGTGCAGCTGGAAGTGCACATCGGATGGCTGCTGCTGCAGGCCCCCAGATGGGTG
TTCAAAGAAGAGGACCCCATCCACCTGAGATGCCACTCTTGGAAGAACACCGCCCTGCACAAAGTGACCTACCTGCAGAAC
GGCAAGGGCAGAAAGTACTTCCACCACAACAGCGACTTCTACATCCCCAAGGCCACCCTGAAGGACTCCGGCTCCTACTTC
TGCAGAGGCCTCGTGGGCAGCAAGAACGTGTCCAGCGAGACAGTGAACATCACCATCACCCAGGGCCTGGCCGTGTCTACC
ATCAGCAGCTTTTTCCCACCCGGCTACCAGGTGTCCTTCTGCCTCGTGATGGTGCTGCTGTTCGCCGTGGACACCGGCCTG
TACTTCAGCGTGAAAACAAACATCAGAAGCAGCACCCGGGACTGGAAGGACCACAAGTTCAAGTGGCGGAAGGACCCCCAG
GACAAGTGAAATTCCGCCCCTCTCCCCGCCCCCCCTCTCCCTCCCCCCCCCCTAACGTTACTGGCCGAAGCCGCTTGGAAT
AAGGCCGGTGTGCGTTTGTCTATATGTTATTTTCCACCATATTGCCGTCTTTTGGCAATGTGAGGGCCCGGAAACCTGGCC
CTGTCTTCTTGACGAGCATTCCTAGGGGTCTTTCCCCTCTCGCCAAAGGAATGCAAGGTCTGTTGAATGTCGTGAAGGAAG
CAGTTCCTCTGGAAGCTTCTTGAAGACAAACAACGTCTGTAGCGACCCTTTGCAGGCAGCGGAACCCCCACCTGGCGACA
GGTGCCTCTGCGGCCAAAAGCCACGTGTATAAGATACACCTGCAAAGGCGGCACAACCCCAGTGCCACGTTGTGAGTTGGA
TAGTTGTGGAAAGAGTCAAATGGCTCTCCTCAAGCGTATTCAACAAGGGGCTGAAGGATGCCCAGAAGGTACCCCATTGTA
TGGGATCTGATCTGGGGCCTCGGTGCACATGCTTTACATGTGTTTAGTCGAGGTTAAAAAAACGTCTAGGCCCCCCGAACC
ACGGGGACGTGGTTTTCCTTTGAAAAACACGATAACCGCCACCATGTACCGGATGCAGCTGCTGAGCTGTATCGCCCTGTC
TCTGGCCCTCGTGACCAACAGCGCCCCTACCAGCAGCAGCACCAAGAAAACCCAGCTGCAGCTGGAACATCTGCTGCTGGA
CCTGCAGATGATCCTGAACGGCATCAACAACTACAAGAACCCCAAGCTGACCCGGATGCTGACCTTCAAGTTCTACATGCC
CAAGAAGGCCACCGAACTGAAACATCTGCAGTGCCTGGAAGAGGAACTGAAGCCCCTGGAAGAAGTGCTGAACCTGGCCCA
GAGCAAGAACTTCCACCTGAGGCCCAGGGACCTGATCAGCAACATCAACGTGATCGTGCTGGAACTGAAAGGCAGCGAGAC
AACCTTCATGTGCGAGTACGCCGACGAGACAGCTACCATCGTGGAATTTCTGAACCGGTGGATCACCTTCTGCCAGAGCAT
CATCAGCACCCTGACCGGCTCCGAGAAGGACGAGCTGTGAGCGGCCGC SEQ ID NO:27

FIG.5A

XXXXXXX = CD33 scFv sequence

XXXXXXX = CAR sequence (CD8 hinge + CD28TM + FceRIg signaling)

XXXXXXX = P2A sequence

XXXXXXX = CD16(158V) sequence

*XXXXXXX* = ERIL-2 sequence

ATG = start codon

Amino acid sequence of CD33 CAR-P2A-CD16:

MDWIWRILFLVGAATGAHSAQPADIQMTQSPSSLSASVGDRVTITCRASESVDNY
GISFMNWFQQKPGKAPKLLIYAASNQGSGVPSRFSGSGSGTDFTLTISSLQPDDF
ATYYCQQSKEVPWTFGQGTKVEIKGGGGSGGGGSGGGGSQVQLVQSGAEVKKPGS
SVKVSCKASGYTFTDYNMHWVRQAPGQGLEWIGYIYPYNGGTYNQKFKSKATIT
ADESTNTAYMELSSLRSEDTAVYYCARGRPAMDYWGQGTLVTVSSAAALSNSIMY
FSHFVPVFLPAKPTTTPAPRPPTPAPTIASQPLSLRPEACRPAAGGAVHTRGLDF
ACFWVLVVVGGVLACYSLLVTVAFIIFWVRLKIQVRKAAITSYEKSDGVYTGLST
RNQETYETLKHEKPPQ<u>GSGATNFSLLKQAGDVEENPGP</u>*MWQLLLPTALLLLVSAG*
*MRTEDLPKAVVFLEPQWYRVLEKDSVTLKCQGAYSPEDNSTQWFHNESLISSQAS*
*SYFIDAATVDDSGEYRCQTNLSTLSDPVQLEVHIGWLLLQAPRWVFKEEDPIHLR*
*CHSWKNTALHKVTYLQNGKGRKYFHHNSDFYIPKATLKDSGSYFCRGLVGSKNVS*
*SETVNITITQGLAVSTISSFFPPGYQVSFCLVMLLFAVDTGLYFSVKTNIRSST*
*RDWKDHKFKWRKDPQDK*\* SEQ ID NO:28

XXXXXXX = CD33 CAR

<u>XXXXXXX</u> = P2A sequence

*XXXXXXX* = CD16(158V)

Amino acid sequence of ERIL-2:

MYRMQLLSCIALSLALVTNSAPTSSSTKKTQLQLEHLLLDLQMILNGINNYKNPK
LTRMLTFKFYMPKKATELKHLCLEEELKPLEEVLNLAQSKNFHLRPRDLISNIN
VIVLELKGSETTFMCEYADETATIVEFLNRWITFCQSIISTLTGSEKDEL\*
SEQ ID NO:8

FIG. 5B

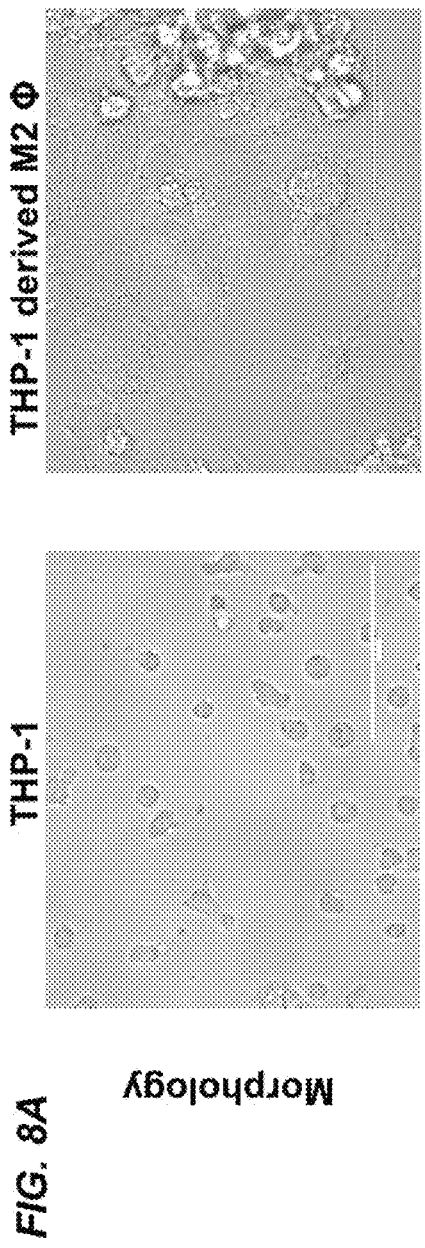
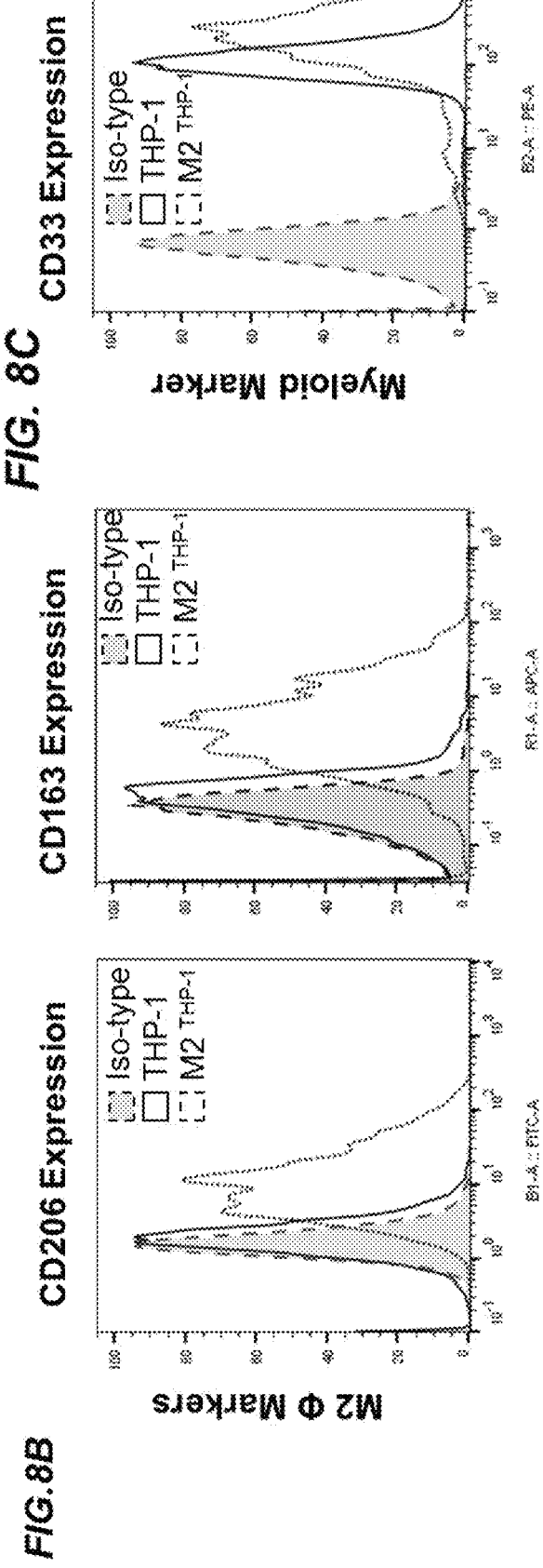
FIG. 8A
FIG. 8B
FIG. 8C

USE OF CD33CAR MODIFIED HIGH AFFINITY NK CELLS (T-HANK) TO REDUCE MYELOID-DERIVED SUPPRESSOR CELLS SUPPRESSOR ACTIVITY (OR REDUCE NEGATIVE IMPACT ON NK CELL ACTIVITY)

This application is a continuation application of U.S. patent application Ser. No. 16/966,868, filed Jul. 31, 2020, now allowed, which is a 35 U.S.C. § 371 U.S. National Stage Entry of International Application No. PCT/US2019/021647, filed Mar. 11, 2019, which claims priority to US Provisional Patent application with the Ser. No. 62/641,915, filed Mar. 12, 2018. The contents of each of these applications are herein incorporated by reference in its entirety.

SEQUENCE LISTING

The instant application contains a Sequence Listing which has been submitted electronically in XML file format and is hereby incorporated by reference in its entirety. Said XML file was created on Sep. 7, 2023, is named 104077.0005US2.xml and is 43,825 bytes in size.

BACKGROUND OF THE INVENTION

Myeloid-derived suppressor cells (MDSCs) are regulators of immune responses in cancer and other pathological conditions, such as myelodysplastic syndrome (MDS) (See, e.g., Bronte et al., NATURE COMMUNICATIONS, 6 Jul. 2016, 7:12150, DOI: 10.1038/ncomms12150; Eksioglu et al., "Novel Therapeutic Approach to Improve Hematopoiesis in low risk MDS by Targeting myeloid-derived suppressor cells with The Fc-engineered CD33 Antibody BI 836858," *Leukemia*. 2017 October; 31(10): 2172-2180. doi: 10.1038/leu.2017.21). Myeloid-derived suppressor cells are a heterogenous group of immune cells from the myeloid lineage (cells that originate from bone marrow stem cells), such as early myeloid progenitors, immature granulocytes, macrophages and dendritic cells at different stages of differentiation. Myeloid-derived suppressor cells strongly expand in pathological situations such as chronic infections and cancer, as a result of an altered haematopoiesis (see, e.g., Eksioglu et al., "Novel Therapeutic Approach to Improve Hematopoiesis in low risk MDS by Targeting myeloid-derived suppressor cells with The Fc-engineered CD33 Antibody BI 836858," *Leukemia*. 2017 October; 31(10): 2172-2180. doi:10.1038/leu.2017.21).

Myeloid-derived suppressor cells are discriminated from other myeloid cell types in which they possess strong immunosuppressive activities rather than immunostimulatory properties. Similar to other myeloid cells, myeloid-derived suppressor cells interact with other immune cell types including T cells, dendritic cells, macrophages and natural killer cells to regulate their functions. Myeloid-derived suppressor cells can suppress both the cytotoxic activities of natural killer (NK) cells and NKT cells, and the adaptive immune response mediated by CD4+ and CD8+ T cells. Although their mechanisms of action are not well understood, clinical and experimental evidence has shown that cancer tissues with high infiltration of myeloid-derived suppressor cells are associated with poor patient prognosis and resistance to therapies.

In mice, Myeloid-derived suppressor cells were historically defined as cells expressing both Gr-1 and CD11b markers (see Bronte et al., NATURE COMMUNICATIONS, 6 Jul. 2016, 7:12150, DOI: 10.1038/ncomms12150). However, subpopulations are known to exist: polymorphonuclear (PMN)-myeloid-derived suppressor cells (CD11b$^+$, Ly6G$^+$, Ly6C$^{lo}$) and monocytic (M)-myeloid-derived suppressor cells (CD11+, Ly6G$^-$, Ly6C$^{hi}$). In human peripheral blood mononuclear cells (PBMC), the equivalent to PMN-myeloid-derived suppressor cells are defined as CD11b$^+$ CD14$^-$ CD15$^+$ or CD11b$^+$ CD14$^-$ CD66b$^+$, and the equivalent to M-myeloid-derived suppressor cells as CD11b$^+$ CD14$^+$ HLA$^-$ DR$^{-/lo}$ CD15$^-$. Immature or early stage myeloid-derived suppressor cells (eMyeloid-derived suppressor cells) are defined as CD33$^+$, Lin$^-$ (including CD3, CD14, CD15, CD19, CD56) and HLA-DR$^-$.

Natural killer (NK) cells are cytotoxic lymphocytes that constitute a major component of the innate immune system. Natural killer (NK) cells, generally representing about 10-15% of circulating lymphocytes, bind and kill targeted cells, including virus-infected cells and many malignant cells, non-specifically with regard to antigen and without prior immune sensitization. Herberman et al., *Science* 214: 24 (1981). Killing of targeted cells occurs by inducing cell lysis. NK cells used for this purpose are isolated from the peripheral blood lymphocyte ("PBL") fraction of blood from the subject, expanded in cell culture in order to obtain sufficient numbers of cells, and then re-infused into the subject. Such autologous NK cells have shown some effectiveness in both ex vivo therapy and in vivo treatment. However, such therapy is limited to autologous contexts, and further complicated by the fact that not all NK cells are cytolytic.

NK-92® is a cytolytic cancer cell line which was discovered in the blood of a subject suffering from a non-Hodgkins lymphoma and then immortalized in vitro. NK-92® cells are derived from NK cells, but lack the major inhibitory receptors that are displayed by normal NK cells, while retaining the majority of the activating receptors. NK-92® cells do not, however, attack normal cells nor do they elicit an unacceptable immune rejection response in humans. Characterization of the NK-92® cell line is disclosed in WO 1998/049268 and U.S. Patent Application Publication No. 2002-0068044. NK-92® cells have been evaluated as a therapeutic agent in the treatment of certain cancers.

Phenotypic changes distinguishing a tumor cell from normal cells derived from the same tissue are often associated with one or more changes in the expression of specific gene products, including the loss of normal cell surface components or the gain of others (i.e., antigens not detectable in corresponding normal, non-cancerous tissue). The antigens which are expressed in neoplastic or tumor cells, but not in normal cells, or which are expressed in neoplastic cells at levels substantially above those found in normal cells, have been termed "tumor-specific antigens" or "tumor-associated antigens." Tumor-specific antigens have been used as targets for cancer immunotherapies. One such therapy utilizes chimeric antigen receptors (CARs) expressed on the surface of immune cells, including T cells and NK cells, to improve cytotoxicity against cancer cells. CARs comprise a single-chain variable fragment (scFv) linked to at least one intracellular signaling domain. The scFv recognizes and binds an antigen on the target cell (e.g., a cancer cell) and triggers effector cell activation. The signaling domains contain immunoreceptor tyrosine-based activation domains (ITAMs) that are important for intracellular signaling by the receptor.

The first generation of CARs used in T-cells contained one cytoplasmic signaling domain. Two versions of first-generation CARs were utilized, one with the signaling domain from the Fc epsilon receptor gamma (FcεRIγ) which contains one ITAM, and the other containing the signaling domain from CD3ζ which contains three ITAMs. In vivo and in vitro studies showed that the CD3ζ CARs were more efficient at tumor eradication than FcεRIγ CARs. See, e.g., Haynes, et al. 2001, *J. Immunology* 166:182-187; Cartellieri, et al. 2010, *J. Biomed and Biotech*, Vol. 2010, Article ID 956304. Additional studies determined that costimulatory signals are required for full activation and proliferation of T cells, and the second and third generation CARs combined multiple signaling domains in to a single CAR in order to enhance efficacy. See Cartellieri, et al. 2010. First generation CARs and the FcεRIγ signaling domains were largely discarded in favor of the new, more efficient CARs using CD3ζ in combination with additional signaling domains. See Hermanson and Kaufman 2015, *Frontiers in Immunol.*, Vol. 6, Article 195.

The instant application provides methods and compositions for reducing the number of myeloid-derived suppressor cells in a subject.

SUMMARY OF THE INVENTION

The present disclosure is directed to methods for reducing the number of myeloid-derived suppressor cells (MDSCs), tumor associated macrophages (TAMs), or both, in a subject suffering from a disease, such as cancer or MDS. In one aspect, the methods described herein comprise administering a therapeutically effective amount of a composition comprising a therapeutic agent that targets an antigen expressed by myeloid-derived suppressor cells to the subject in need of treatment. In some embodiments, the therapeutic agent targets an antigen expressed by CD33 positive myeloid-derived suppressor cells or TAMs. In some embodiments, the therapeutic agent comprises an antigen binding protein (ABP) that specifically binds to an antigen expressed by CD33 positive myeloid-derived suppressor cells or TAMs. For example, in some embodiments, the antigen binding protein is an antibody or fragment thereof, or an scFv, that specifically binds CD33. In some embodiments, the composition comprises a recombinant cell that expresses an ABP that specifically binds CD33. In some embodiments, the recombinant cell is a T cell. In some embodiments, the recombinant cell is an NK cell. In some embodiments, the recombinant cell is an NK-92® cell described herein. The methods described herein provide the unexpected advantage of reducing or eliminating myeloid-derived suppressor cells in the bone marrow environment that negatively affect immune cell function (i.e., immunosuppression), and at the same time also reduce or eliminate CD33 positive tumor cells associated with acute myelogenous leukemia (AML) or myelodysplastic syndrome (MDS).

In some embodiments, the recombinant cell is a genetically modified cell. In some embodiments, the recombinant cell is a genetically modified NK-92® cell or cell line engineered to express a chimeric antigen receptor (CAR) on the surface of the NK-92® cell(s). In some embodiments, the CAR targets an antigen expressed by myeloid-derived suppressor cells. In one embodiment, the antigen is CD33. In some embodiments, the CAR targets a tumor-associated antigen. In one embodiment, the tumor-associated antigen is CD33. In some embodiments, the CAR comprises an amino acid sequence having at least 90%, 91%, 92%, 93%, 94%, 95%, 96%, 97%, 98%, 99%, 99.5%, or 99.9% identity to an antigen binding protein that specifically binds CD33. In some embodiments, the antigen binding protein is an antibody or antigen binding fragment thereof that specifically binds CD33. In some embodiments, the antigen binding protein is an scFv that specifically binds CD33. In some embodiments, the CAR comprises an amino acid sequence having at least 90%, 91%, 92%, 93%, 94%, 95%, 96%, 97%, 98%, 99%, 99.5%, or 99.9% identity to SEQ ID NO:15 (CD33 scFv). In some embodiments, the CAR comprises an amino acid sequence having at least 90%, 91%, 92%, 93%, 94%, 95%, 96%, 97%, 98%, 99%, 99.5%, or 99.9% identity to SEQ ID NO:16 (complete CD33 CAR). In some embodiments, the CAR comprises an amino acid sequence having at least 90%, 91%, 92%, 93%, 94%, 95%, 96%, 97%, 98%, 99%, 99.5%, or 99.9% identity to SEQ ID NO:24 (light chain variable domain). In some embodiments, the CAR comprises an amino acid sequence having at least 90%, 91%, 92%, 93%, 94%, 95%, 96%, 97%, 98%, 99%, 99.5%, or 99.9% identity to SEQ ID NO:25 (heavy chain variable domain). In some embodiments, the CAR comprises an amino acid sequence having at least 90%, 91%, 92%, 93%, 94%, 95%, 96%, 97%, 98%, 99%, 99.5%, or 99.9% identity to SEQ ID Nos: 18, 19, 20, 21, 22, and/or 23 (CDR sequences).

In some embodiments, the recombinant cell is a genetically modified T cell or cell line engineered to express a chimeric antigen receptor (CAR) on the surface of the T cell(s). In some embodiments, the CAR targets an antigen expressed by myeloid-derived suppressor cells's. In one embodiment, the antigen is CD33. In some embodiments, the CAR targets a tumor-associated antigen. In one embodiment, the tumor-associated antigen is of CD33.

In some embodiments, the CAR comprises an intracellular signaling domain from the Fc epsilon receptor gamma (FcεRIγ). In one embodiment, the intracellular signaling domain of FcεRIγ comprises the amino acid sequence of SEQ ID NO: 1. In some embodiments, the CAR comprises a hinge region from CD8. In some embodiments, the CAR comprises a transmembrane domain from CD28. In one embodiment, the CAR is transiently expressed by the NK-92® cell or T cell.

To date, FcεRIγ-containing CARs have not been utilized in NK-92® cells, other NK cell lines, or endogenous NK cells because other signaling domains (e.g., CD3ζ) were determined to be more efficient, especially when combined with additional signaling domains (second and third generation CARs). The present disclosure provides the surprising finding that NK-92® cells expressing a CAR comprising an intracellular domain from FcεRIγ have equal or higher cytotoxic activity against cancer cells expressing the antigen recognized by the CAR than NK-92® cells expressing CARs with a CD3ζ signaling domain alone or in combination with other signaling domains (i.e., second or third generation CARs).

In one aspect, the recombinant cell is transfected with a DNA construct comprising one or more nucleic acid sequences that encode: (i) an antigen binding protein that specifically binds CD33 (such as an anti-CD33 ScFv); (ii) a CD8 hinge region; (iii) a CD28 transmembrane region; (iv) an intracellular signaling domain from the Fc epsilon receptor gamma (FcεRIγ); (v) a high affinity CD16 (158V) receptor; and (vi) an IL-2 variant that is targeted to the endoplasmic reticulum (erIL-2). In some embodiments, the recombinant cell is transfected with a DNA construct comprising or consisting of the nucleic acid sequence shown in FIG. 7.

In some embodiments, the method comprises administering a combination of (i) an antigen binding protein (ABP) that specifically binds an antigen expressed by myeloid-derived suppressor cells (or TAMs) and (ii) a genetically modified cell that expresses an ABP that specifically binds an antigen expressed by myeloid-derived suppressor cells (or TAMs) to the subject. In some embodiments, the method comprises administering a combination of (i) an antigen binding protein (ABP) that specifically binds CD33 and a (ii) genetically modified cell that expresses an ABP that specifically binds CD33 to the subject. In some embodiments, the ABP is an antibody or fragment thereof that specifically binds CD33. In some embodiments, the combination of ABP and the genetically modified cell expressing an ABP that specifically bind CD33 comprise the same or substantially similar immunoglobulin heavy and light chain variable regions. In some embodiments, the combination of ABP and the genetically modified cell that expresses an ABP that specifically bind CD33 comprise different immunoglobulin heavy and light chain variable regions. In some embodiments, the combination comprises an ABP and a genetically modified NK-92® cell(s) that expresses an ABP that specifically binds CD33 on the surface of MDSCs, TAMs or both.

In some embodiments, the method further comprises administering to the subject a second therapeutic agent. In some embodiments, the second therapeutic agent is a genetically modified cell or cell line that expresses a CAR on the cell surface. In some embodiments, the CAR expressed by the second genetically modified cell or cell line targets a tumor-associated antigen. In one embodiment, the tumor-associated antigen is selected from the group consisting of CD19, CD20, NKG2D ligands, CS1, GD2, CD138, EpCAM, HER-2, EBNA3C, GPA7, CD244, CA-125, MUC-1, ETA, MAGE, CEA, CD52, CD30, MUC5AC, c-Met, EGFR, FAB, WT-1, PSMA, NY-ESO1, and CD33.

In some embodiments, the NK-92® cell or T cell line is transformed by a nucleic acid encoding a chimeric antigen receptor (CAR) with a cytoplasmic domain of FcεRIγ, wherein the CAR is expressed on the surface of the NK-92® cell or T cell. In one embodiment, the nucleic acid is RNA. In one embodiment, the nucleic acid is DNA.

In some embodiments, the NK-92® cell is further modified to express at least one cytokine or variant thereof. In one embodiment, the at least one cytokine is transiently expressed by the NK-92® cell. In one embodiment, the at least one cytokine is stably expressed by the NK-92® cell.

In some embodiments, the NK-92® cell is further modified to express a suicide gene. In one embodiment, the suicide gene is thymidine kinase. Without being bound by theory, it is believed that expression of a suicide gene will prevent uncontrolled proliferation of the NK-92® cells by providing a mechanism for killing the cells upon introduction of a stimulus.

The instant disclosure also describes methods of treating cancer in a patient in need thereof, comprising administering to the patient a therapeutically effective amount of CAR-expressing NK-92® cells or CAR-expressing T cells as described herein.

In another aspect, compositions comprising an ABP that specifically binds to an antigen expressed by myeloid-derived suppressor cells and/or TAMs are described. In some embodiments, the composition comprises an ABP that specifically binds to CD33 positive myeloid-derived suppressor cells and/or TAMs. In some embodiments, the composition comprises an ABP that specifically binds to CD33. In some embodiments, the composition comprises a genetically modified NK-92® cell or NK-92® cell line engineered to express a CAR on their cell surface that targets or specifically binds to CD33. In some embodiments, the composition comprises a genetically modified T cell or T cell line engineered to express a CAR on their cell surface that targets or specifically binds to CD33. In some embodiments, the composition comprises a combination of (i) an ABP that specifically binds to CD33, and (ii) a genetically modified cell or cell line engineered to express a CAR that targets or specifically binds to CD33 on the surface of the cell(s). In one embodiment, the combination comprises (i) an ABP that specifically binds to CD33, and (ii) a genetically modified NK-92® cell or NK-92® cell line engineered to express a CAR on their cell surface that targets or specifically binds to CD33 expressed by MDSC and/or TAMs.

It is understood that administering an ABP in combination with a modified T cell or NK-92® cell described herein may result in improved functionality of the modified T cell or NK-92® cell. For example, antibody-dependent cell-mediated cytotoxicity (ADCC) associated with administration of the ABP may lead to increased reduction of myeloid-derived suppressor cells (or TAMs) when the ABP is administered in combination with the modified NK-92® cell. In some embodiments, the combination results in an increased reduction of myeloid-derived suppressor cells (or TAMs) compared to administration of the ABP or modified cell alone (e.g., the combination results in fewer myeloid-derived suppressor cells that infiltrate a tissue or tumor than administration of either the ABP or modified T cell or NK-92® cell alone).

Also described is the use of a composition described herein for the treatment of a disease described herein. In some embodiments, use of a composition comprising an ABP that specifically binds to an antigen expressed by myeloid-derived suppressor cells and/or TAMs for treating a disease is described. In some embodiments, the use comprises a composition comprising an ABP that specifically binds to an antigen expressed by myeloid-derived suppressor cells and/or TAMs. In some embodiments, the use comprises a composition comprising an ABP that specifically binds to CD33 positive myeloid-derived suppressor cells and/or TAMs. In some embodiments, the use comprises a composition comprising an ABP that specifically binds to CD33. In some embodiments, the ABP is an antibody of functional fragment thereof that specifically binds to CD33. In some embodiments, the use comprises a composition comprising a genetically modified NK-92® cell or NK-92® cell line engineered to express a CAR that targets or specifically binds to CD33 on the surface of myeloid-derived suppressor cells and/or TAMs. In some embodiments, the use comprises a composition comprising a genetically modified T cell or T cell line engineered to express a CAR that targets or specifically binds to CD33 on the surface of myeloid-derived suppressor cells and/or TAMs. In some embodiments, the use comprises a composition comprising a combination of (i) an ABP that specifically binds to CD33, and (ii) a genetically modified cell or cell line engineered to express a CAR that targets or specifically binds to CD33 on the surface of myeloid-derived suppressor cells and/or TAMs and/or abnormal or tumor cells. In one embodiment, the use comprises a composition comprising (i) an ABP that specifically binds to CD33, and (ii) a genetically modified NK-92® cell or NK-92® cell line engineered to express a CAR that targets or specifically binds to CD33 on the surface of myeloid-derived suppressor cells and/or TAMs. In one embodiment, the combination comprises (i) an ABP that specifically binds to CD33, and (ii) a genetically modified T cell or T cell line engineered to express a CAR that targets or specifically binds to CD33 on the surface of myeloid-derived suppressor cells.

In some embodiments, a medicament for treating a disease described herein is provided. In some embodiments, the medicament comprises a composition described herein.

BRIEF DESCRIPTION OF THE DRAWINGS

The objects, features and advantages of the present disclosure will be more readily appreciated upon reference to the following disclosure when considered in conjunction with the accompanying drawings.

FIG. 4 shows that myeloid-derived suppressor cells can negatively affect proliferation of NK-92® (aNK™) cells, and that NK-92® cells with reduced expression of CD96/TIGIT (CD96/TIGIT-KO aNK™ cells) are more resistant to myeloid-derived suppressor cell-mediated inhibition of degranulation.

FIG. 5A shows the codon-optimized nucleic acid sequence (SEQ ID NO: 27) of one embodiment of a tricistronic expression cassette used to transfect recombinant NK-92® cells as described herein. FIG. 5B shows the amino acid sequence of the polypeptides encoded by the nucleic acid sequences in the expression cassette. Amino acid sequence of CD33 CAR-P2A-CD16: SEQ ID NO: 28. Amino acid sequence of erIL2: SEQ ID NO: 8.

FIG. 8A shows morphological characterization of M2 like macrophages differentiated from the THP-1 human monocytic cell line. FIG. 8B shows cell surface expression of M2 macrophage markers from THP-1 cells differentiated into M2 like macrophages by flow cytometry. FIG. 8C shows CD33 expression on THP-1 and M2 cells (differentiated from THP-1 cells) by flow cytometry.

DEFINITIONS

Figure 1:
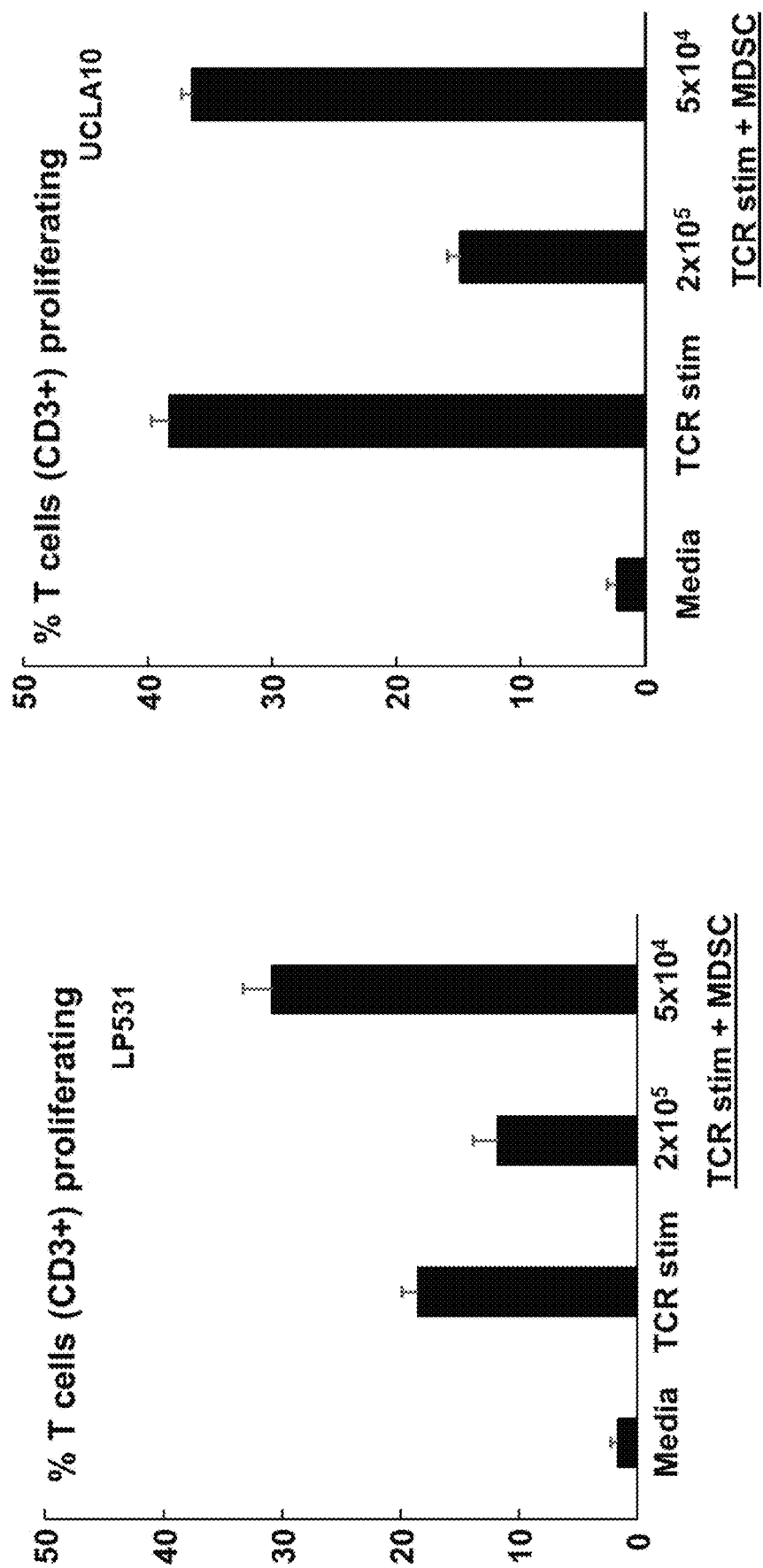
FIG. 1 shows myeloid-derived suppressor cells inhibit human T cell proliferation. Myeloid-derived suppressor cells (UCLA donor 2) were derived using a CD11b selection kit. CD11b-selected cells were cultured for four days with GM-CSF (5 ng/ml), then harvested and frozen. PBMC from two donors (LP531 and UCLA10) were thawed, labeled with CFSE, then stimulated (200,000/well) with anti-CD3/CD28 beads, and cultured with allogeneic myeloid-derived suppressor cells (UCLA donor 2) at two cell concentrations. T cells exhibiting reduced CFSE were identified as proliferating and represented as % T cells proliferating.

Unless defined otherwise, all technical and scientific terms used herein have the same meaning as commonly understood by one of ordinary skill in the art to which this disclosure belongs.

In this specification and in the claims that follow, reference will be made to a number of terms that shall be defined to have the following meanings:

The terminology used herein is for the purpose of describing particular embodiments only and is not intended to be limiting. As used herein, the singular forms "a", "an" and "the" are intended to include the plural forms as well, unless the context clearly indicates otherwise.

The term "and/or" is equivalent to one or both. For example, the term "MDSC and/or TAM" is equivalent to the term "MDSC, TAM, or both".

All numerical designations, e.g., pH, temperature, time, concentration, amounts, and molecular weight, including ranges, are approximations which are varied (+) or (−) by increments of 0.1 or 1.0, where appropriate. It is to be understood, although not always explicitly stated, that all numerical designations may be preceded by the term "about." The term "about" as used herein means that the value can vary by +10%, 5%, or 1%.

It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed subject matter. "Consisting of" shall mean excluding more than trace amount of other ingredients and substantial method steps recited. Embodiments defined by each of these transition terms are within the scope of this disclosure.

As used herein, "immunotherapy" refers to the use of NK-92® cells, modified or unmodified, naturally occurring or modified NK cell or T-cell, whether alone or in combination, and which are capable of inducing cytotoxicity when contacting a target cell.

As used herein, "natural killer (NK) cells" are cells of the immune system that kill target cells in the absence of a specific antigenic stimulus, and without restriction according to major histocompatibility complex (MHC) class. Target cells may be tumor cells or cells harboring a virus. NK cells are characterized by the presence of CD56 and the absence of CD3 surface markers.

The term "endogenous NK cells" is used to refer to NK cells derived from a donor (or the patient), as distinguished from the NK-92® cell line. Endogenous NK cells are generally heterogeneous populations of cells within which NK cells have been enriched. Endogenous NK cells may be intended for autologous or allogeneic treatment of a patient.

The term "NK-92" refers to natural killer cells derived from the highly potent unique cell line described in Gong et al. (1994), rights to which are owned by NantKwest® (hereafter, "NK-92® cells"). The immortal NK cell line was originally obtained from a patient having non-Hodgkin's lymphoma. Unless indicated otherwise, the term "NK-92®" is intended to refer to the original NK-92® cell lines as well as NK-92® cell lines that have been modified (e.g., by introduction of exogenous genes). NK-92® cells and exemplary and non-limiting modifications thereof are described in U.S. Pat. Nos. 7,618,817; 8,034,332; 8,313,943; 9,181,322; 9,150,636; and published U.S. application Ser. No. 10/008, 955, all of which are incorporated herein by reference in their entireties, and include wild type NK-92®, NK-92®-CD16, NK-92®-CD16-7, NK-92®-CD16-ζ, NK-92®-CD16(F176V), NK-92® MI, and NK-92® CI. NK-92® cells are known to persons of ordinary skill in the art, to whom such cells are readily available from NantKwest, Inc.

The term "aNK" refers to an unmodified natural killer cells derived from the highly potent unique cell line described in Gong et al. (1994), rights to which are owned by NantKwest® (hereafter, "aNK™ cells"). The term "haNK" refers to natural killer cells derived from the highly potent unique cell line described in Gong et al. (1994), rights to which are owned by NantKwest®, modified to express CD16 on the cell surface (hereafter, "CD16+ NK-92® cells" or "HANK® cells"). In some embodiments, the CD16+ NK-92® cells comprise a high affinity CD16 receptor on the cell surface. The term "taNK" refers tp natural killer cells derived from the highly potent unique cell line described in Gong et al. (1994), rights to which are owned by NantKwest®, modified to express a chimeric antigen receptor (hereafter, "CAR-modified NK-92® cells" or "TANK® cells"). The term "t-haNK" refers to natural killer cells derived from the highly potent unique cell line described in Gong et al. (1994), rights to which are owned by NantkWest®, modified to express CD 16 on the cell surface and to express a chimeric antigen receptor (hereafter, "CAR-modified CD16+ NK-92® cells" or "t-haNK™ cells"). In some embodiments, the t-haNK™ cells express a high affinity CD16 receptor on the cell surface.

A "modified NK-92 cell" refers to an NK-92® cell that expresses an exogenous gene or protein, such as an Fc receptor, a CAR, a cytokine (such as IL-2 or IL-12), and/or a suicide gene. In some embodiments, the modified NK-92® cell comprises a vector that encodes for a transgene, such as an Fc receptor, a CAR, a cytokine (such as IL-2 or IL-12), and/or a suicide gene. In one embodiment, the modified NK-92® cell expresses at least one transgenic protein.

As used herein, "non-irradiated NK-92 cells" are NK-92® cells that have not been irradiated. Irradiation renders the cells incapable of growth and proliferation. It is envisioned that the NK-92® cells will be irradiated at the treatment facility or some other point prior to treatment of a patient, since the time between irradiation and infusion should be no longer than four hours in order to preserve optimal activity. Alternatively, NK-92® cells may be prevented from proliferating by another mechanism.

As used herein, "inactivation" of the NK-92® cells renders them incapable of growth. Inactivation may also relate to the death of the NK-92® cells. It is envisioned that the NK-92@cells may be inactivated after they have effectively purged an ex vivo sample of cells related to a pathology in a therapeutic application, or after they have resided within the body of a mammal a sufficient period of time to effectively kill many or all target cells residing within the body. Inactivation may be induced, by way of non-limiting example, by administering an inactivating agent to which the NK-92® cells are sensitive.

As used herein, the terms "cytotoxic" and "cytolytic," when used to describe the activity of effector cells such as NK-92® cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK-92® cells is due to cytolysis.

The term "kill" with respect to a cell/cell population is directed to include any type of manipulation that will lead to the death of that cell/cell population.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FCγR) bind to the IgG class of antibodies. FCγRIII-A (also called CD16) is a low affinity Fc receptor bind to IgG antibodies and activate ADCC. FCγRIII-A are typically found on NK cells. NK-92® cells do not express FCγRIII-A. Fc-epsilon receptors (FcεR) bind to the Fc region of IgE antibodies.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92® cell is targeted to cells expressing certain antigens on the cell surface, based on the specificity of the scFv domain. The scFv domain can be engineered to recognize any antigen, including tumor-specific antigens and virus-specific antigens. For example, CD19CAR recognizes CD19, a cell surface marker expressed by some cancers.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences described herein.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information web-site. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, an expectation (E) of 10, and the BLOSUM62 scoring matrix (see Henikoff and Henikoff, Proc. Natl. Acad. Sci. USA 89:10915-10919, 1992).

Identical sequences include 100% identity of a polynucleotide comprising a first nucleotide sequence to a polynucleotide comprising a second nucleotide sequence over the entire length of one or both nucleotide sequences. Such sequences can be referred to as "fully identical" with respect to each other herein. In some aspects, where a first sequence is referred to as "substantially identical" with respect to a second sequence, the two sequences can be fully complementary, or they may be at least about 50, 60, 70, 80, 81, 82, 83, 84, 85, 86, 87, 88, 89, 90, 91, 92, 93, 94, 95, 96, 97, 98, or 99% identical to each other. To determine the percent identity of two nucleotide sequences described herein, the default settings of BLASTN described above can be used.

The term "express" refers to the production of a gene product (e.g., a protein). The term "transient" when referring to expression means a polynucleotide is not incorporated into the genome of the cell. The term "stable" when referring to expression means a polynucleotide is incorporated into the genome of the cell, or a positive selection marker (i.e., an exogenous gene expressed by the cell that confers a benefit under certain growth conditions) is utilized to maintain expression of the transgene.

The term "cytokine" or "cytokines" refers to the general class of biological molecules which affect cells of the immune system. Exemplary cytokines include but are not limited to interferons and interleukins (IL) in particular IL-2, IL-12, IL-15, IL-18 and IL-21. In preferred embodiments, the cytokine is IL-2.

As used herein, the term "vector" refers to a non-chromosomal nucleic acid comprising an intact replicon such that the vector may be replicated when placed within a permissive cell, for example by a process of transformation. A vector may replicate in one cell type, such as bacteria, but have limited or no ability to replicate in another cell, such as mammalian cells. Vectors may be viral or non-viral. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In one embodiment, the vector is a viral vector, e.g. adenovirus. Viral vectors are well known in the art.

As used herein, the term "targeted," when referring to protein expression, is intended to include, but is not limited to, directing proteins or polypeptides to appropriate destinations in the cell or outside of it. The targeting is typically achieved through signal peptides or targeting peptides, which are a stretch of amino acid residues in a polypeptide chain. These signal peptides can be located anywhere within a polypeptide sequence, but are often located on the N-terminus. Polypeptides can also be engineered to have a signal peptide on the C-terminus. Signal peptides can direct a polypeptide for extracellular section, location to plasma membrane, golgi, endosomes, endoplasmic reticulum, and other cellular compartments. For example, polypeptides with a particular amino acid sequence on their C-terminus (e.g., KDEL; SEQ ID NO: 26) are retained in the ER lumen or transported back the ER lumen.

As used herein, the term "target," when referring to targeting of a tumor, refers to the ability of NK-92® cells to recognize and kill a tumor cell (i.e., target cell). The term "targeted" in this context refers, for example, to the ability of a CAR expressed by the NK-92® cell to recognize and bind to a cell surface antigen expressed by the tumor.

As used herein, the term "transfect" refers to the insertion of nucleic acid into a cell. Transfection may be performed using any means that allows the nucleic acid to enter the cell. DNA and/or mRNA may be transfected into a cell. Preferably, a transfected cell expresses the gene product (i.e., protein) encoded by the nucleic acid.

The term "suicide gene" refers to a transgene that allows for the negative selection of cells expressing that transgene. A suicide gene is used as a safety system, allowing the cells expressing the gene to be killed by introduction of a selective agent. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (see also, for example, Yazawa K, Fisher W E, Brunicardi F C: Current progress in suicide gene therapy for cancer. World J. Surg. 2002 July; 26(7):783-9). In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

The term "antigen binding protein" refers to a protein that specifically binds a target antigen or ligand with high affinity and/or specificity. Examples of antigen binding proteins include receptors that bind ligands, antibodies and immunologically functional fragments thereof, and peptibodies. An "immunologically functional fragment" of an antibody or immunoglobulin chain (heavy or light chain) antigen binding protein, refers to a portion of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab')2, Fv domain antibodies and single-chain antibodies, and a single chain variable fragment (scFv), and can be derived from any mammalian source, including but not limited to human, mouse, rat, camelid or rabbit. Functional portions of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen binding protein can include nonprotein components.

The term "antibody" refers to an intact immunoglobulin of any isotype, or a fragment thereof that can compete with the intact antibody for specific binding to the target antigen, and includes chimeric, humanized, fully human, and bispecific antibodies. An intact antibody generally comprises at least two full-length heavy chains and two full-length light chains, but in some instances can include fewer chains such as antibodies naturally occurring in camelids which can comprise only heavy chains. Antibodies can be derived solely from a single source, or can be "chimeric," such that different portions of the antibody are derived from two different antibodies. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also includes peptibodies.

The term "specific binding" refers to high avidity binding of an ABP to the antigen of interest, and typically does not include ABPs that bind to or show cross-reactivity to other antigens or epitopes. The term "avidity" refers to the overall stability or strength of binding between an antibody and its cognate antigen. Avidity includes the sum of the strengths of individual antibody-antigen interactions, and is controlled by antibody epitope affinity, the valence of both the antigen and antibody, and the structural arrangement of the interacting parts. The term "affinity" refers to the strength of binding of a single molecule to its ligand, for example, the strength of an individual interaction between a single binding site on an antibody and its target epitope. Avidity and Affinity are typically measured by the equilibrium dissociation constant ($K_D$), which can be used to evaluate the strengths of bimolecular interactions. For example, the binding of an antibody to its antigen is a reversible process, and the rate of the binding reaction is proportional to the concentrations of the reactants. At equilibrium, the rate of [antibody] [antigen] complex formation is equal to the rate of dissociation into its components [antibody]+[antigen]. The measurement of the reaction rate constants can be used to define an equilibrium or affinity constant (1/KD). Thus, the lower the dissociation constant, the higher the avidity or affinity, and the stronger the interaction between the antibody and its target antigen. The ABPs described herein can have $K_D$ values in the low micromolar ($10^{-6}$) to picomolar ($10^{-12}$) range.

The term "subject' refers to a non-human animal, including mammals, such as cats, dogs, cows, horses, pigs, sheep, and goats, and humans. The term subject also refers to a patient in need of treatment for a disease described herein.

The term "tumor associated macrophage" (TAM) refers to bone marrow-derived blood monocytes/monocytic MDSC (M-MDSC) that are recruited to tumors and differentiate into TAMs.

DETAILED DESCRIPTION OF THE INVENTION

After reading this description, it will become apparent to one skilled in the art how to implement various alternative embodiments and alternative applications. However, not all embodiments of the present disclosure are described herein. It will be understood that the embodiments presented here are presented by way of an example only, and not limitation.

As such, this detailed description of various alternative embodiments should not be construed to limit the scope or breadth of the present disclosure as set forth below.

It is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

Titles or subtitles may be used in the specification for the convenience of a reader, which are not intended to influence the scope of the present disclosure. Additionally, some terms used in this specification are more specifically defined below.

NK-92® Cells

The NK-92® cell line is a unique cell line that was discovered to proliferate in the presence of interleukin 2 (IL-2). Gong et al., *Leukemia* 8:652-658 (1994). These cells have high cytolytic activity against a variety of cancers. The NK-92® cell line is a homogeneous cancerous NK cell population having broad anti-tumor cytotoxicity with predictable yield after expansion. Phase I clinical trials have confirmed its safety profile.

The NK-92® cell line exhibits the $CD56^{bright}$ CD2, CD7, CD11a, CD28, CD45, and CD54 surface markers. It furthermore does not display the CD1, CD3, CD4, CD5, CD8, CD10, CD14, CD16, CD19, CD20, CD23, and CD34 markers. Growth of NK-92® cells in culture is dependent upon the presence of interleukin 2 (rIL-2), with a dose as low as 1 IU/mL being sufficient to maintain proliferation. IL-7 and IL-12 do not support long-term growth, nor do other cytokines tested, including IL-1$\alpha$, IL-6, tumor necrosis factor $\alpha$, interferon $\alpha$, and interferon $\gamma$. NK-92® has high cytotoxicity even at a low effector:target (E:T) ratio, e.g. 1:1. Gong, et al., supra.

For purposes of this disclosure and unless indicated otherwise, the term "NK-92" is intended to refer to the original NK-92® cell lines as well as NK-92® cell lines, clones of NK-92® cells, and NK-92® cells that have been modified (e.g., by introduction of exogenous genes. In some embodiments, the NK-92® cell expresses an Fc receptor.

Myeloid-Derived Suppressor Cells (MDSCs) and Tumor Associated Macrophages

As described in Kumar et al. (*Trends Immunol.* 2016 March; 37(3): 208-220. doi:10.1016/j.it.2016.01.004), myeloid-derived suppressor cells (MDSC) are one of the major components of the tumor microenvironment. MDSC have potent immune suppressive activity. Studies in both mice and humans have identified two different types of MDSC: polymorphonuclear MDSC (PMN-MDSC), which are morphologically and phenotypically similar to neutrophils; and monocytic MDSC (M-MDSC), which are similar to monocytes. In tumors, M-MDSC are more prominent than PMN-MDSC, and M-MDSC rapidly differentiate to tumor associated macrophages (TAM). In cancer, TAM originate primarily from BM-derived blood monocytes/M-MDSC recruited to tumors. In experiments in which MDSC were transplanted into tumors or spleens of mice, the MDSC differentiated slowly to macrophages (MΦ) and dendritic cells (DCs) in the spleen, whereas MDSC differentiated rapidly to TAM in tumors. Id. A recent study suggests that hypoxia in the tumor microenvironment (TME) may play a role in the differentiation of M-MDSC to TAM. (see Kumar V, et al. CD45 phosphatase regulates the fate of myeloid cells in tumor microenvironment by inhibiting STAT3 activity Immunity. 2016). Thus, the terms MDSC and TAM can be used interchangeably in this disclosure.

Tumor-Associated Macrophages (TAMs)

Macrophages are large, specialized, professional phagocytic cells that arise from monocytes in response to chemical stimuli received from the surrounding environment. Macrophage plasticity and diversity allow their classification along with a M1-M2 polarization axis. Tumors use chemokine signals to draw monocytes and tissue-resident macrophages into the tumor microenvironment, where the cells become tumor-associated macrophages (TAMs). Once believed to be wholly supportive of cancerous growth, these cells also play important roles in protection against disease. Tumor-associated macrophages (TAMs) usually display a M2-like phenotype, associated with pro-tumoral features whereas M1 macrophages exert antitumor functions. M2 macrophages exert diverse functions, such as tissue repair, matrix remodeling, angiogenesis, immunosuppression, and favor tumor growth. Therefore, targeting TAMs would be an efficient way to promote tumor regression.

The main stimuli for M2 polarization are IL-4, IL-13, IL-10, and transforming growth factor $\beta$ (TGF$\beta$). When these stimuli are bound to respective receptors (ILR4$\alpha$, ILR10, or TGF$\beta$R), the cells are induced to an M2-like macrophage phenotype. These stimuli activate several transcription factors, such as IRF/STAT family members, and the inhibitory NF$\kappa$B homodimer (p50-p50). Further, HIF2 influences M2 polarization. Macrophages with a polarized M2-like phenotype produce specific cytokines (IL-10), chemokines (CCL5, CCL17, CCL18, CCL22), and other proteins (CD163, CD206, Arg1, MMP-9, Fizz-1, Ym-1, and PD-L1). (*Front Immunol.* 2017; 8: 828).

Vectors

Described herein are vectors for transfecting cells to produce the modified cells described herein. In one embodiment, the vectors described herein are transient expression vectors. Exogenous transgenes introduced using such vectors are not integrated in the nuclear genome of the cell; therefore, in the absence of vector replication, the foreign transgenes will be degraded or diluted over time.

In one embodiment, the vectors described herein allow for stable transfection of cells. In one embodiment, the vector allows incorporation of the transgene(s) into the genome of the cell. In one embodiment, the vectors have a positive selection marker. Positive selection markers include any genes that allow the cell to grow under conditions that would kill a cell not expressing the gene. Non-limiting examples include antibiotic resistance, e.g. geneticin (Neo gene from Tn5).

In one embodiment, the vector is a plasmid vector. In one embodiment, the vector is a viral vector. As would be understood by one of skill in the art, any suitable vector can be used. Suitable vectors are well-known in the art.

In some embodiments, the cells are transfected with mRNA encoding the protein of interest (e.g., a CAR). Transfection of mRNA results in transient expression of the protein. In one embodiment, transfection of mRNA into NK-92® cells is performed immediately prior to administration of the cells. In one embodiment, "immediately prior" to administration of the cells refers to between about 15 minutes and about 48 hours prior to administration. Preferably, mRNA transfection is performed about 5 hours to about 24 hours prior to administration.

Fc Receptors

In some embodiments, the NK-92® cells are modified to express at least one Fc receptor, such that the at least one Fc receptor is displayed on the cell surface of the NK-92® cell. Fc receptors bind to the Fc portion of antibodies. Several Fc receptors are known, and differ according to their preferred ligand, affinity, expression, and effect following binding to the antibody.

TABLE 1

Illustrative Fc receptors

| Receptor name | Principal antibody ligand | Affinity for ligand | Cell distribution | Effect following binding to antibody |
|---|---|---|---|---|
| FcγRI (CD64) | IgG1 and IgG3 | High (Kd~$10^{-9}$ M) | Macrophages Neutrophils Eosinophils Dendritic cells | Phagocytosis Cell activation Activation of respiratory burst Induction of microbe killing |
| FcγRIIA (CD32) | IgG | Low (Kd > $10^{-7}$ M) | Macrophages Neutrophils Eosinophils Platelets Langerhans cells | Phagocytosis Degranulation (eosinophils) |
| FcγRIIB1 (CD32) | IgG | Low (Kd > $10^{-7}$ M) | B Cells Mast cells | No phagocytosis Inhibition of cell activity |
| FcγRIIB2 (CD32) | IgG | Low (Kd > $10^{-7}$ M) | Macrophages Neutrophils Eosinophils | Phagocytosis inhibition of cell activity |
| FcγRIIIA (CD16a) | IgG | Low (Kd > $10^{-6}$ M) | NK cells Macrophages (certain tissues) | Induction of antibody-dependent cell-mediated cytotoxicity (ADCC) Induction of cytokine release by macrophages |
| FcγRIIIB (CD16b) | IgG | Low (Kd > $10^{-6}$ M) | Eosinophils Macrophages Neutrophils Mast cells Follicular dendritic cells | Induction of microbe killing |
| FcεRI | IgE | High (Kd~$10^{-10}$ M) | Mast cells Eosinophils Basophils Langerhans cells Monocytes | Degranulation Phagocytosis |
| FcεRII (CD23) | IgE | Low (Kd > $10^{-7}$ M) | B cells Eosinophils Langerhans cells | Possible adhesion molecule IgE transport across human intestinal epithelium Positive-feedback mechanism to enhance allergic sensitization (B cells) |
| FcαRI (CD89) | IgA | Low (Kd > $10^{-6}$ M) | Monocytes Macrophages Neutrophils Eosinophils | Phagocytosis Induction of microbe killing |
| Fcα/μR | IgA and IgM | High for IgM, Mid for IgA | B cells Mesangial cells Macrophages | Endocytosis Induction of microbe killing |
| FcRn | IgG |  | Monocytes Macrophages Dendritic cells Epithelial cells Endothelial cells Hepatocytes | Transfers IgG from a mother to fetus through the placenta Transfers IgG from a mother to infant in milk Protects IgG from degradation |

In some embodiments NK-92® cells are modified to express an Fc receptor protein on the cell surface.

In some embodiments, the Fc receptor is CD16. For purposes of this disclosure, specific amino acid residues of CD16 are designated with reference to SEQ ID NO:10, or to SEQ ID NO:9, which differs at one position relative to SEQ ID NO:10. Thus, an amino acid residue "at position 158" of a CD16 polypeptide is the amino acid residue that corresponds to position 158 of SEQ ID NO:10 (or SEQ ID NO:9), when the CD16 polypeptide and SEQ ID NO:10 are maximally aligned. In some embodiments, NK-92® cells are modified to express a human CD16 that has a phenylalanine at position 158 of the mature form of the protein, e.g., SEQ ID NO:9. In typical embodiments, NK-92® cells are modified to express a high affinity form of human CD16 having a valine at position 158 of the mature form of the protein, e.g., SEQ ID NO:10. Position 158 of the mature protein corresponds to position 176 of the CD16 sequence that includes the native signal peptide. In some embodiments, a CD16 polypeptide is encoded by a polynucleotide that encodes the precursor (i.e., has a native signal peptide) polypeptide sequence of SEQ ID NO:11 or of SEQ ID NO:12. Thus, in one embodiment, the Fc receptor comprises FcγRIII-A (CD16). In some embodiments, the NK-92® cells are genetically modified to express an Fc receptor encoding a polypeptide having at least 90% sequence identity with SEQ ID NO:9 (FcγRIII-A or CD16 having a phenylalanine at position 158 (F-158); or at least 90% identity to SEQ ID NO:10 (CD16 having a valine at position 158 (F158V), higher affinity form).

In some embodiments, a polynucleotide encoding a CD16 polypeptide has at least about 70% polynucleotide sequence identity with a polynucleotide sequence encoding a full-length, including signal peptide, naturally occurring CD16 that has a phenylalanine at position 176 of the full-length CD16 (which corresponds to position 158 of the mature CD16 protein). In some embodiments, a polynucleotide encoding a CD16 polypeptide has at least about 70% polynucleotide sequence identity with a polynucleotide sequence encoding a full-length, including the signal peptide, naturally occurring CD16 that has a valine at position 176 (which corresponds to position 158 of the mature protein). In some embodiments, a polynucleotide encoding CD16 has at least 70%, 80%, 90%, or 95% identity to SEQ ID NO:13 and comprises a codon encoding valine at the position of the polynucleotide that encodes position 176 of the full-length, including the signal peptide, CD16 polypeptide. In some embodiments, a polynucleotide encoding CD16 comprises SEQ ID NO:13, but with a codon encoding valine at position 176 of the full-length CD16.

In some embodiments, the CD16 polynucleotide encodes a polypeptide having at least 70%, 80%, 90%, or 95% identity to SEQ ID NO:9 or SEQ ID NO:10. In some embodiments, the polynucleotide encodes a polypeptide having at least 70% 80%, 90%, or 95% identity to SEQ ID NO:10 and comprises a valine at position 158 as determined with reference to SEQ ID NO:10. In some embodiments the polynucleotide encodes SEQ ID NO:10. In some embodiments, a CD16 polynucleotide encodes an extracellular domain of CD16 with or without the signal sequence, or any other fragment of a full length CD16, or a chimeric receptor encompassing at least partial sequence of CD16 fused to an amino acid sequence of another protein. In other embodiments, an epitope tag peptide, such as FLAG, myc, polyhistidine, or V5 can be added to the amino terminal domain of the mature polypeptide to assist in cell surface detection by using anti-epitope tag peptide monoclonal or polyclonal antibodies.

In some embodiments, homologous CD16 polynucleotides may be about 150 to about 700, about 750, or about 800 polynucleotides in length, although CD16 variants having more than 700 to 800 polynucleotides are within the scope of the disclosure.

Homologous polynucleotide sequences include those that encode polypeptide sequences coding for variants of CD16. Homologous polynucleotide sequences also include naturally occurring allelic variations related to SEQ ID NO:13. Transfection of an NK-92® cell with any polynucleotide encoding a polypeptide having the amino acid sequence shown in either SEQ ID. NO: 9 or SEQ ID NO: 10, a naturally occurring variant thereof, or a sequence that is at least 70% identical, or at least 80%, 90%, or 95% identical to SEQ ID. NO: 9 or SEQ ID NO: 10 is within the scope of the disclosure. In some embodiments, homologous polynucleotide sequences encode conservative amino acid substitutions in SEQ ID. NO: 9 or SEQ ID NO: 10. In some embodiments, NK-92® cells are transfected using a degenerate homologous CD16 polynucleotide sequence that differs from a native polynucleotide sequence, but encodes the same polypeptide.

In other examples, cDNA sequences having polymorphisms that change the CD16 amino acid sequences are used to modify the NK-92® cells, such as, for example, the allelic variations among individuals that exhibit genetic polymorphisms in CD16 genes. In other examples, CD16 genes from other species that have a polynucleotide sequence that differs from the sequence of SEQ ID NO: 13 are used to modify NK-92® cells.

Variant polypeptides can be made using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

In some embodiments, a polynucleotide encoding a CD16 is mutated to alter the amino acid sequence encoding for CD16 without altering the function of CD16. For example, polynucleotide substitutions leading to amino acid substitutions at "non-essential" amino acid residues can be made in SEQ ID NO:9 or SEQ ID NO:10.

Conservative substitutions in SEQ ID. NO:9 or SEQ ID NO:10, whereby an amino acid of one class is replaced with another amino acid of the same class, fall within the scope of the disclosed CD16 variants as long as the substitution does not materially alter the activity of the polypeptide. Conservative substitutions are well known to one of skill in the art. Non-conservative substitutions that affect (1) the structure of the polypeptide backbone, such as a (3-sheet or α-helical conformation, (2) the charge, (3) the hydrophobicity, or (4) the bulk of the side chain of the target site can modify CD16 polypeptide function or immunological identity. Non-conservative substitutions entail exchanging a member of one of these classes for another class. Substitutions may be introduced into conservative substitution sites or more preferably into non-conserved sites.

In some embodiments, CD16 polypeptide variants are at least 200 amino acids in length and have at least 70% amino acid sequence identity, or at least 80%, or at least 90% identity to SEQ ID NO:9 or SEQ ID NO:10. In some embodiments, CD16 polypeptide variants are at least 225 amino acid in length and have at least 70% amino acid sequence identity, or at least 80%, or at least 90% identity to SEQ ID NO:9 or SEQ ID NO:10. In some embodiments, CD16 polypeptide variants have a valine at position 158 as determined with reference to SEQ ID NO:10.

In some embodiments a nucleic acid encoding a CD16 polypeptide may encode a CD16 fusion protein. A CD16 fusion polypeptide includes any portion of CD16 or an entire CD16 fused with a non-CD16 polypeptide. Fusion polypeptides are conveniently created using recombinant methods. For example, a polynucleotide encoding a CD16 polypeptide such as SEQ ID NO:9 or SEQ ID NO:10 is fused in-frame with a non-CD16 encoding polynucleotide (such as a polynucleotide sequence encoding a signal peptide of a heterologous protein). In some embodiment, a fusion polypeptide may be created in which a heterologous polypeptide sequence is fused to the C-terminus of CD16 or is positioned internally in the CD16. Typically, up to about 30% of the CD16 cytoplasmic domain may be replaced. Such modification can enhance expression or enhance cytotoxicity (e.g., ADCC responsiveness). In other examples, chimeric proteins, such as domains from other lymphocyte activating receptors, including but not limited to Ig-a, Ig-B, CD3-e, CD3-d, DAP-12 and DAP-10, replace a portion of the CD16 cytoplasmic domain.

Fusion genes can be synthesized by conventional techniques, including automated DNA synthesizers and PCR amplification using anchor primers that give rise to complementary overhangs between two consecutive gene fragments that can subsequently be annealed and reamplified to generate a chimeric gene sequence (Ausubel, 2002). Many vectors are commercially available that facilitate sub-cloning CD16 in-frame to a fusion moiety.

Antigen Binding Proteins

In some embodiments, the antigen binding proteins described herein specifically bind an antigen expressed by myeloid-derived suppressor cells. In some embodiments, the antigen binding proteins described herein specifically bind an antigen expressed by CD33 positive (CD33$^+$) myeloid-derived suppressor cells. In one embodiment, the antigen binding proteins described herein specifically CD33.

In some embodiments, the ABP comprises domains that are each capable of binding to two different antigens (i.e., the ABP is bispecific for two antigens). For example, in some embodiments, the ABP comprises a bispecific antibody, or fragment thereof, that binds two antigens. In one embodiment, the ABP is bispecific for a first antigen expressed by myeloid-derived suppressor cells and a second antigen expressed by tumor cells (e.g., a tumor-specific antigen). For example, in some embodiments, the ABP is bispecific for CD33 and a tumor-specific antigen. In some embodiments, the two antigens that bind the ABP are different. For example, in one embodiment, the bispecific ABP specifically binds CD33 and CD19. In some embodiments, the two antigens that bind the ABP are the same, or comprise different epitopes from the same antigen. For example, in one embodiment, the ABP binds CD33 expressed by myeloid-derived suppressor cells and binds CD33 expressed by tumor cells.

Chimeric Antigen Receptors

In one aspect, NK-92® cells or T cells are engineered to express a CAR on the cell surface. In some embodiments, the cytoplasmic domain of the CAR comprises a signaling domain of FcεRIγ. In one embodiment, the cytoplasmic domain of the CAR consists of a signaling domain of FcεRIγ. In one embodiment, the FcεRIγ signaling domain is substantially identical to SEQ ID NO:1. In one embodiment, the FcεRIγ signaling domain comprises an amino acid sequence having at least 70%, 75% 80%, 85%, 90%, 91%, 92%, 93%, 94%, 95%, 96%, 97%, 98%, or 99% identity to SEQ ID NO:1. In one embodiment, the FcεRIγ signaling domain comprises or consists of or consists essentially of an amino acid sequence having at least about 70%, 75% 80%, 85%, 90%, 95%, 96%, 97%, 98%, or 99% sequence identity to the amino acid sequence of SEQ ID NO.: 1. In one embodiment, the FcεRIγ signaling domain comprises or consists of or consists essentially of the amino acid sequence of SEQ ID NO.: 1. In one embodiment, the cytoplasmic domain does not comprise any signaling domain other than the FcεRIγ signaling domain.

The CAR may comprise any suitable transmembrane domain. In one aspect, the CAR comprises a transmembrane domain of CD28. In one embodiment, the CD28 transmembrane domain is substantially identical to SEQ ID NO:5. In one embodiment, the CD28 transmembrane domain comprises or consists of or consists essentially of the amino acid sequence of SEQ ID NO.: 5. In one embodiment, the CD28 transmembrane domain comprises or consists of or consists essentially of an amino acid sequence having at least about 70%, 75% 80%, 85%, 90%, 91%, 92%, 93%, 94%, 95%, 96%, 97%, 98%, or 99% sequence identity to the amino acid sequence of SEQ ID NO.: 5. In one embodiment, the transmembrane domain is selected from the group consisting of CD8 transmembrane domain, 4-1BB transmembrane domain, and FcεRIγ transmembrane domain.

The CAR may comprise any suitable hinge region. In one aspect, the CAR comprises a hinge region of CD8. In one embodiment, the CD28 transmembrane domain is substantially identical to SEQ ID NO:4. In one embodiment, the CD8 hinge region comprises or consists of or consists essentially of the amino acid sequence of SEQ ID NO.: 4. In one embodiment, the CD8 hinge region comprises or consists of or consists essentially of an amino acid sequence having at least about 70%, 75% 80%, 85%, 90%, 91%, 92%, 93%, 94%, 95%, 96%, 97%, 98%, or 99% sequence identity to the amino acid sequence of SEQ ID NO.: 4.

In some embodiments, the CAR is specific for an antigen expressed by myeloid-derived suppressor cells. In one embodiment, the CAR is specific for an antigen expressed by CD33 positive myeloid-derived suppressor cells. In one embodiment, the CAR is specific for CD33.

In some embodiments, the CAR comprises an ABP that is bispecific for two antigens, as described herein. For example, in some embodiments, the CAR comprises a bispecific antibody, or fragment thereof, that binds two antigens. In one embodiment, the CAR comprises an ABP that is bispecific for a first antigen expressed by myeloid-derived suppressor cells and a second tumor-specific antigen. For example, in some embodiments, the CAR comprises an ABP that is bispecific for CD33 and a tumor-specific antigen. In some embodiments, the CAR comprises an ABP that specifically binds two different antigens. For example, in one embodiment, the CAR comprises a bispecific ABP specifically binds CD33 and CD19. In some embodiments, the CAR comprises an ABP that specifically binds the same or similar antigens, or specifically binds epitopes from the same antigen. For example, in one embodiment, the ABP binds CD33 expressed by myeloid-derived suppressor cells and binds CD33 expressed by tumor cells.

In one embodiment, the CAR is specific for a tumor-specific antigen. Tumor-specific antigens are described, by way of non-limiting example, in US2013/0189268; WO 1999024566 A1; U.S. Pat. No. 7,098,008; and WO 2000020460 A1, each of which is incorporated herein by reference in its entirety. Tumor-specific antigens include, without limitation, NKG2D ligands, CS1, GD2, CD138, EpCAM, EBNA3C, GPA7, CD244, CA-125, ETA, MAGE, CAGE, BAGE, HAGE, LAGE, PAGE, NY-SEO-1, GAGE, CEA, CD52, CD30, MUC5AC, c-Met, EGFR, FAB, WT-1, PSMA, NY-ESO1, AFP, CEA, CTAG1B, CD19, and CD33. Additional non-limiting tumor-associated antigens, and the malignancies associated therewith, can be found in Table 2.

In some embodiments, the NK-92® cells are modified to express at least one Fc receptor described herein and at least one chimeric antigen receptor (CAR), such that the at least one Fc receptor and the at least one CAR are displayed on the cell surface of the NK-92® cell. In one embodiment, the Fc receptor comprises FcγRIII-A (CD16) and the CAR is a CD33CAR described herein. In some embodiments, the NK-92® cells are genetically modified to express an Fc receptor encoding a polypeptide having at least 90% sequence identity with SEQ ID NO:9 (FcγRIII-A or CD16 having a phenylalanine at position 158 (F-158); or at least 90% identity to SEQ TD NO: 10 (CD16 having a valine at position 158 (F158V), higher affinity form) and a CD33CAR described herein.

TABLE 2

Tumor-Specific Antigens and Associated Malignancies

| Target antigen | Associated malignancy |
| --- | --- |
| α-Folate receptor | Ovarian cancer |
| CAIX | Renal cell carcinoma |
| CD19 | B-cell malignancies |
| | CLL |
| | B-ALL |
| | ALL; ALL post-HSCT |
| | Lymphoma; Refractory Follicular Lymphoma; B-NHL |
| | Leukemia |
| | B-cell malignancies; B-cell malignancies post-HSCT |
| | B-lineage lymphoid malignancies post-UCBT |
| | B-cell malignancies, CLL, B-NHL |
| CD19/CD20 | Lymphoblastic leukemia |
| CD20 | Lymphomas |
| | B-cell malignancies |
| | B-cell lymphomas |
| | Mantle cell lymphoma |
| | indolent B-NHL |
| | Leukemia |
| CD22 | B-cell malignancies |
| CD30 | Lymphomas; Hodgkin lymphoma |
| CD33 | AML |
| CD44v7/8 | Cervical carcinoma |
| CD138 | Multiple myeloma |
| CD244 | Neuroblastoma |
| CEA | Breast cancer |
| | Colorectal cancer |
| CS1 | Multiple myeloma |
| EBNA3C | EBV positive T cells |
| EGP-2 | Multiple malignancies |
| EGP-40 | Colorectal cancer |
| EpCAM | Breast carcinoma |
| erb-B2 | Colorectal cancer |
| | Breast and others |
| | Prostate cancer |
| erb-B 2, 3, 4 | Breast and others |
| FBP | Ovarian cancer |
| Fetal acetylcholine receptor | Rhabdomyosarcoma |
| GD2 | Neuroblastoma |
| GD3 | Melanoma |
| GPA7 | Melanoma |
| Her2 | Breast carcinoma |
| | Ovarian cancer |
| | Tumors of epithelial origin |
| Her2/neu | Medulloblastoma |
| | Lung malignancy |
| | Advanced osteosarcoma |
| | Glioblastoma |
| IL-13R-a2 | Glioma |
| | Glioblastoma |
| | Medulloblastoma |
| KDR | Tumor neovasculature |
| k-light chain | B-cell malignancies (B-NHL, CLL) |
| LeY | Carcinomas |
| | Epithelial derived tumors |
| L1 cell adhesion molecule | Neuroblastoma |
| MAGE-A1 | Melanoma |
| Mesothelin | Various tumors |
| MUC1 | Breast, Ovary |
| NKG2D ligands | Various tumors |
| Oncofetal antigen (h5T4) | Various tumors |
| PSCA | Prostate carcinoma |
| PSMA | Prostate/tumor vasculature |
| TAA targeted by mAb IgE | Various tumors |
| TAG-72 | Adenocarcinomas |
| VEGF-R2 | Tumor neovasculature |

In one embodiment, the CAR targets an antigen associated with a specific cancer type. In one embodiment, the cancer is selected from the group consisting of leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

CARs can be engineered as described, for example, in Patent Publication Nos. WO 2014039523; US 20140242701; US 20140274909; US 20130280285; and WO 2014099671, each of which is incorporated herein by reference in its entirety.

Cytokines

In one embodiment, NK-92® cells are modified to express at least one cytokine. In particular, the at least one cytokine is IL-2, IL-12, IL-15, IL-18, IL-21, or a variant thereof. In preferred embodiments, the cytokine is IL-2 or a variant thereof. In certain embodiments, the IL-2 is a variant that is targeted to the endoplasmic reticulum.

In one embodiment, the IL-2 is cloned and expressed with a signal sequence that directs the IL-2 to the endoplasmic reticulum (erIL-2). This permits expression of IL-2 at levels sufficient for autocrine activation, but without releasing IL-2 extracellularly. See Konstantinidis et al "Targeting IL-2 to the endoplasmic reticulum confines autocrine growth stimulation to NK-92® cells" *Exp Hematol.* 2005 February; 33(2):159-64.

Suicide Gene

The term "suicide gene" refers to a transgene that allows for the negative selection of cells expressing the suicide gene. A suicide gene is used as a safety system, allowing cells expressing the gene to be killed by introduction of a selective agent. This is desirable in case the recombinant gene causes a mutation leading to uncontrolled cell growth, or the cells themselves are capable of such growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene. Typically, the suicide gene encodes for a protein that has no ill effect on the cell but, in the presence of a specific compound, will kill the cell. Thus, the suicide gene is typically part of a system.

In one embodiment, the suicide gene is active in NK-92® cells. In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

In another embodiment, the suicide gene is cytosine deaminase, which is toxic to cells in the presence of 5-fluorocytosine. Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." *Blood.* 1998 Jul. 15; 92(2):672-82.

In another embodiment, the suicide gene is cytochrome P450, which is toxic in the presence of ifosfamide or cyclophosphamide. See, e.g. Touati et al. "A suicide gene therapy combining the improvement of cyclophosphamide tumor cytotoxicity and the development of an anti-tumor immune response." *Curr Gene Ther.* 2014; 14(3):236-46.

In another embodiment, the suicide gene is iCasp9. Di Stasi, (2011) "Inducible apoptosis as a safety switch for adoptive cell therapy." *N Engl J Med* 365: 1673-1683. See also Morgan, "Live and Let Die: A New Suicide Gene Therapy Moves to the Clinic" *Molecular Therapy* (2012); 20: 11-13. iCasp9 induces apoptosis in the presence of a small molecule, AP1903. AP1903 is biologically inert small molecule, that has been shown in clinical studies to be well tolerated, and has been used in the context of adoptive cell therapy.

Transgene Expression

Transgenes can be engineered into an expression vector by any mechanism known to those of skill in the art. Where multiple transgenes are to be inserted into a cell, transgenes may be engineered into the same expression vector or a different expression vector.

In some embodiments, the cells are transfected with mRNA encoding the transgenic protein to be expressed.

Transgenes and mRNA can be introduced into the NK-92® cells using any transfection method known in the art, including, by way of non-limiting example, infection, electroporation, lipofection, nucleofection, or "gene-gun."

Treatment

Described herein are methods of treating patients with antigen binding proteins that specifically bind CD33. In some embodiments, the CD33 is expressed by myeloid-derived suppressor cells. In some embodiments, the ABP is administered alone or with an adjuvant that stimulates the immune response. In some embodiments, a modified cell expressing the ABP that specifically binds CD33 is administered to the patient. In one embodiment, the modified cell is a T cell or NK-92® cell. In some embodiments, the ABP (alone or with an adjuvant) is administered in combination with a modified cell that expresses an ABP that specifically binds CD33 is administered to the patient. In some embodiments, the ABP is an antibody or fragment thereof, or an scFv. In some embodiments, the modified T cell or NK-92® cell expresses a CAR that targets CD33. In some embodiments, the combination of an ABP that binds CD33 and a modified T cell or NK-92® cell that expresses an ABP to CD33 results in increased reduction of (or cytotoxicity) of myeloid-derived suppressor cells by the modified T cell or NK-92® cells compared to administration of the ABP or modified cell alone.

In one embodiment, the patient is suffering from a disease associated with myeloid-derived suppressor cells infiltration, such as chronic inflammation, cancer, infection, autoimmune diseases, trauma, or graft versus host disease. In one embodiment, the patient is suffering from a disease associated with myeloid-derived suppressor cells infiltration. In some embodiments, the CAR expressed by the T cell or NK-92® cell is specific for an antigen expressed on the surface of myeloid-derived suppressor cells.

Modified T cells and NK-92® cells can be administered to an individual by absolute numbers of cells, e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) T cells or NK-92® cells per injection, or any ranges between any two of the numbers, end points inclusive. In other embodiments, cells can be administered to an individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) cells per kilogram of the individual, or any ranges between any two of the numbers, end points inclusive. In other embodiments, the total dose may calculated by m² of body surface area, including about $1\times10^{11}$, $1\times10^{10}$, $1\times10^9$, $1\times10^8$, $1\times10^7$, per m², or any ranges between any two of the numbers, end points inclusive. The average person is about 1.6 to about 1.8 m². In a preferred embodiment, between about 1 billion and about 3 billion T cells or NK-92® cells are administered to a patient.

The modified T cells and NK-92® cells described herein can be administered once to a patient or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In one embodiment, where the T cells or NK-92® cells express a suicide gene, the patient is administered an agent to trigger modified cell death. In one embodiment, the agent is administered at a time point after administration of the modified cells that is sufficient for the modified T cells or NK-92® cells to kill target cells.

In one embodiment, the modified NK-92® cells are irradiated prior to administration to the patient. Irradiation of NK-92® cells is described, for example, in U.S. Pat. No. 8,034,332, which is incorporated herein by reference in its entirety. In one embodiment, modified NK-92@cells that have not been engineered to express a suicide gene are irradiated.

Diseases

The methods and compositions described herein are useful for treating diseases related to immune disorders associated with myeloid-derived suppressor cells. In some embodiments, the disease is a stem cell malignancy or a myelodysplastic syndrome (MDS). In some embodiments, the disease is associated with cytological dysplasia, ineffective hematopoiesis, or a disease that can progress to acute myeloid leukemia (AML). In some embodiments, the disease is associated with infiltration of myeloid-derived suppressor cells into a tissue, such as tumor or cancer tissue. In some embodiments, the disease is chronic inflammation, cancer, infection, an autoimmune disease, trauma, or graft versus host disease.

EXAMPLES

The following examples are for illustrative purposes only and should not be interpreted as limitations of the claimed subject matter. There are a variety of alternative techniques and procedures available to those of skill in the art which would similarly permit one to successfully perform the claimed subject matter.

Example 1

Figure 2:
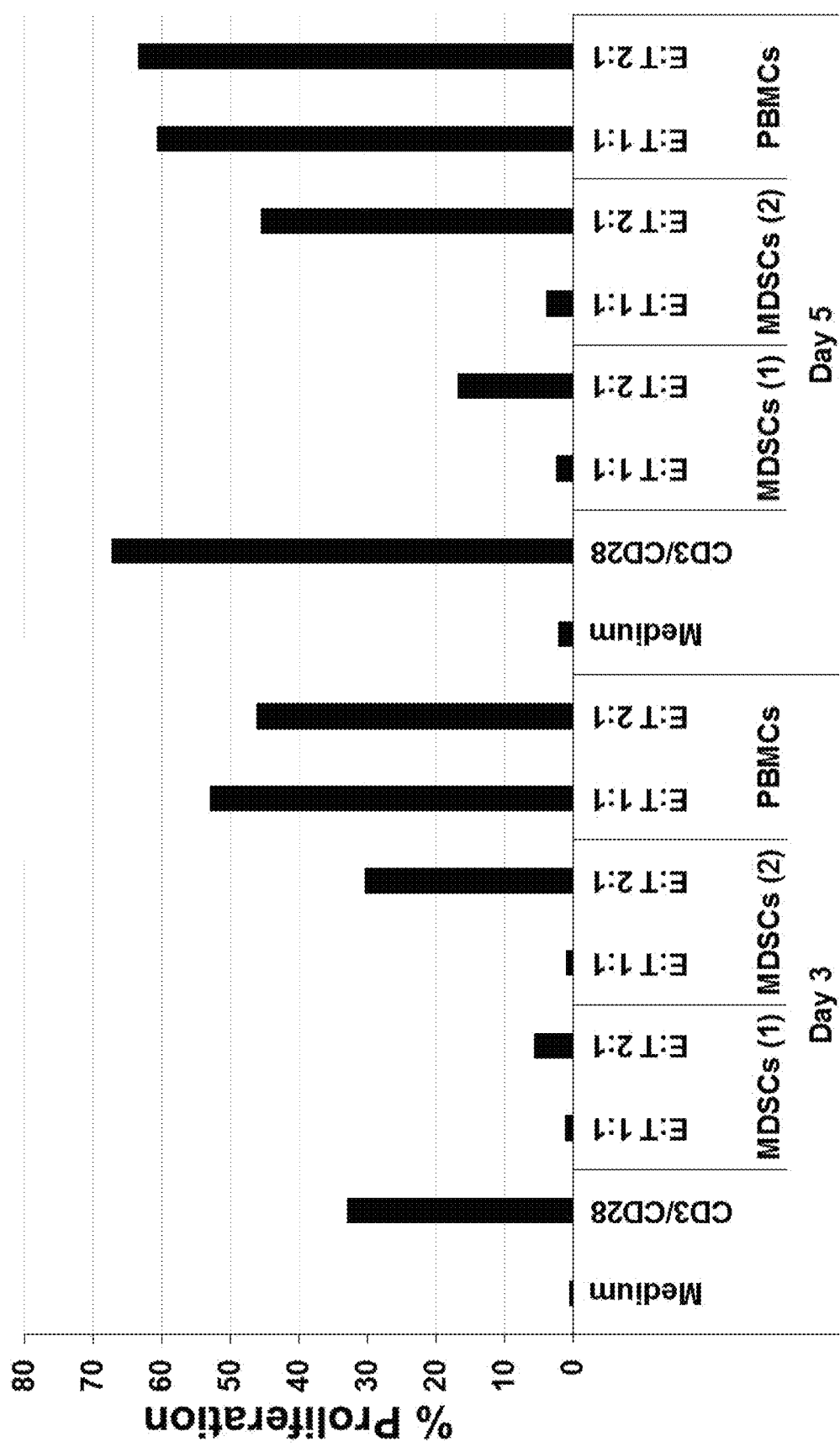
FIG. 2 shows myeloid-derived suppressor cells inhibit human T cell proliferation.

This example shows that myeloid-derived suppressor cells inhibit human T cell proliferation. As shown in FIG. 1 and FIG. 2, myeloid-derived suppressor cells inhibit human T cell proliferation.

Methods: Myeloid-derived suppressor cells were generated by purifying the CD11b+ cells from healthy donor PBMCs and culturing the cells for 7 days in the presence of GM-CSF (10 ng/ml) and IL-6 (10 ng/ml) (see Lechner et al J Immunol 2010). Myeloid-derived suppressor cells (UCLA donor 2) were derived using a CD11b selection kit. CD11b-selected cells were cultured for four days with GM-CSF (5 ng/ml), then harvested and frozen. PBMC from two donors (LP531 and UCLA10) were thawed, labeled with CFSE, then stimulated (200,000/well) with anti-CD3/CD28 beads, and cultured with allogeneic myeloid-derived suppressor cells (UCLA donor 2) at two cell concentrations. T cells exhibiting reduced CFSE were identified as proliferating and represented as % T cells proliferating. The results are shown in FIG. 1 and FIG. 2.

Example 2

Figure 3:
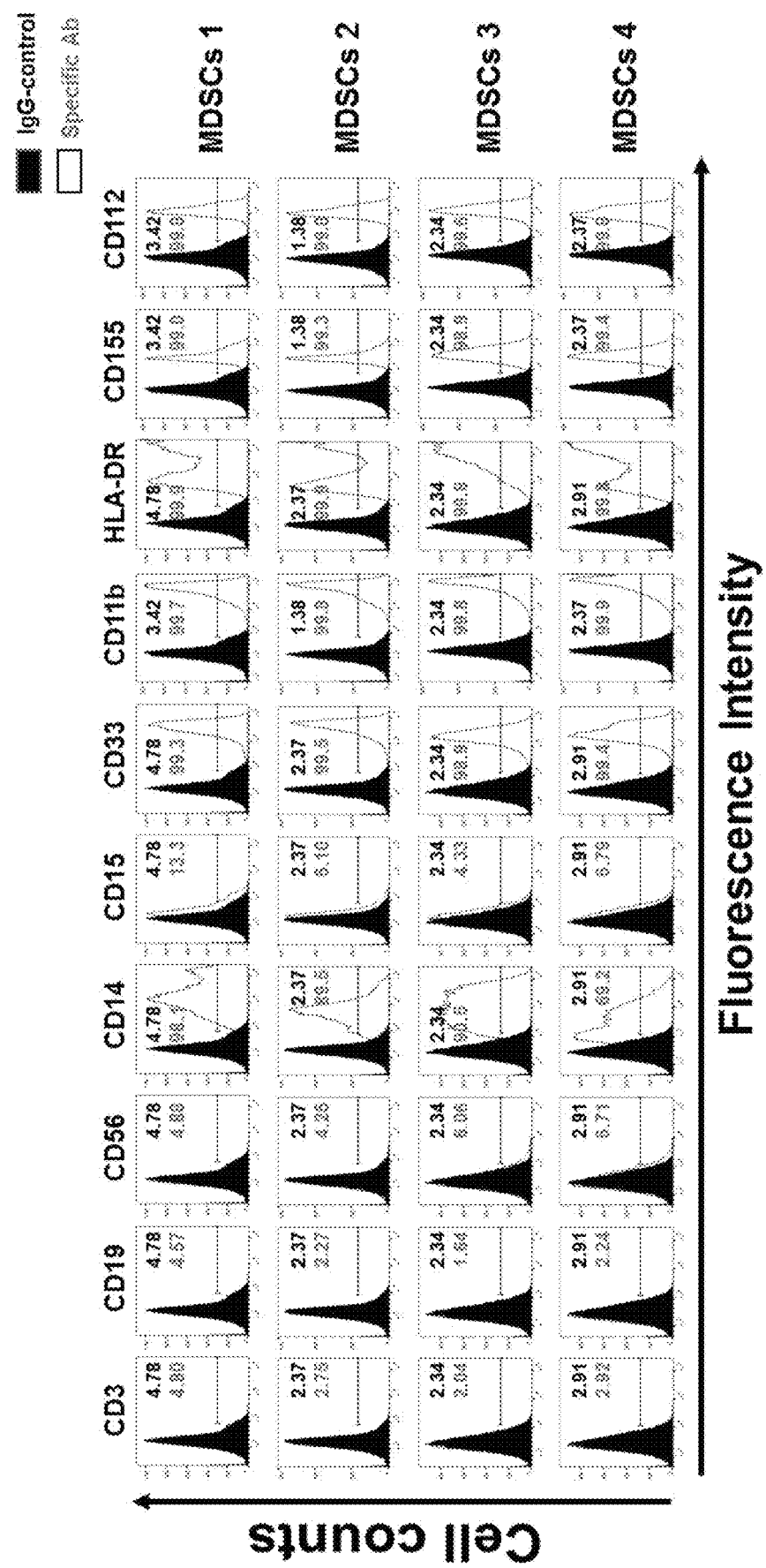
FIG. 3 shows a representative immunophenotype of myeloid-derived suppressor cells. This data confirms that myeloid-derived suppressor cells are CD33 positive.

This example shows the immunophenotype of myeloid-derived suppressor cells. As shown in FIG. 3, myeloid-derived suppressor cells are CD33 positive.

Example 3

This example shows that myeloid-derived suppressor cells can negatively affect proliferation of NK-92® (aNK™) cells, and that NK-92® cells with reduced expression of CD96/TIGIT (CD96/TIGIT-KO aNK™ cells) are more resistant to myeloid-derived suppressor cell-mediated inhibition of degranulation (FIG. 4).

Example 4

FIG. 5A shows the codon-optimized nucleic acid sequence in the expression cassette used to transfect NK-92® cells for expression of CD33 CAR. FIG. 5B shows the amino acid sequence of the polypeptides encoded by the nucleic acid sequences in the expression cassette.

Example 5

This example shows that cells that are resistant to specific lysis (cytotoxicity) by control (unmodified) NK-92® cells can be efficiently killed by NK-92® cells that express a CAR that specifically binds to CD33.

Figure 6A:
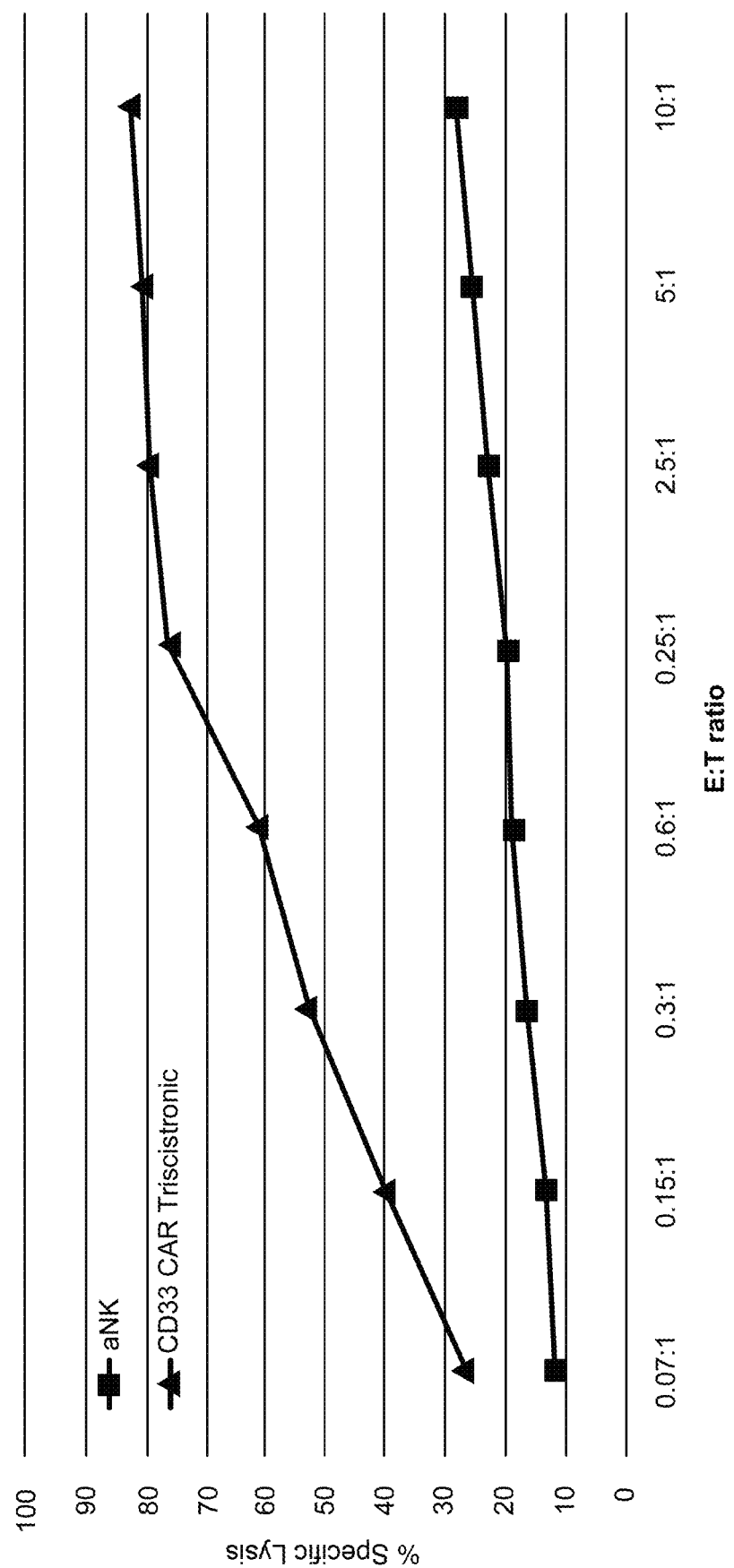
FIG. 6A provides in vitro data showing that CD33 positive (CD33+) THP-1 cells are relatively resistant to cytotoxicity (specific lysis) by control NK-92® (aNK™) cells, whereas there is a high percentage of specific lysis when THP-1 cells are cultured with NK-92® cells that express a CAR that specifically binds CD33 (CD33-CAR/NK-92® cells).
Figure 6B:
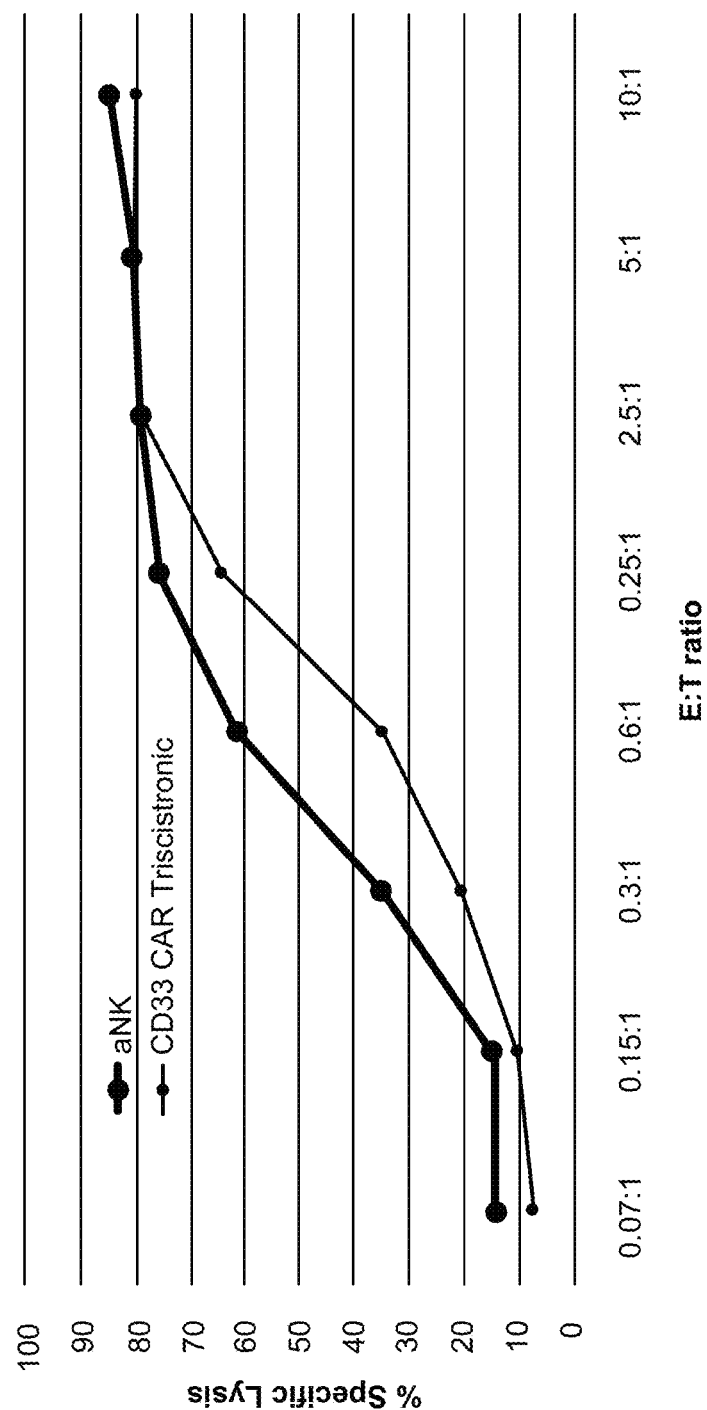
FIG. 6B provides in vitro data showing that K562 cells are efficiently killed by both control aNK™ cells and CD33-CAR/NK-92® cells.

FIG. 6A provides in vitro data showing that CD33 positive (CD33+) THP-1 cells are relatively resistant to cytotoxicity (specific lysis) by control NK-92® (aNK™) cells, whereas there is a high percentage of specific lysis when THP-1 cells are cultured with NK-92® cells that express a CAR that specifically binds CD33 (CD33-CAR/NK-92® cells). FIG. 6B provides in vitro data showing that K562 cells are efficiently killed by both control aNK™ cells and CD33-CAR/NK-92® cells.

Figure 7:
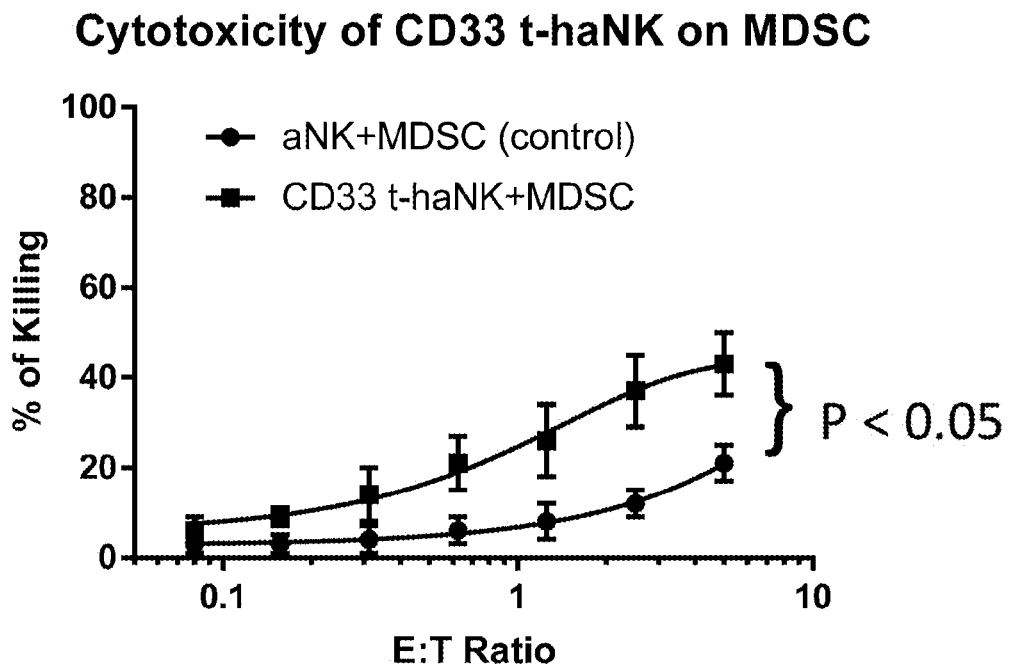
FIG. 7 shows the result of a cytotoxicity assay of effector CD33 t-haNK™ cells against MDSC target cells. Effector to target cell ratio (E:T) is shown on the X-axis and percent (%) killing of PMBC derived MDSC targets is shown on the Y-axis.

In addition, CD33-CAR/t-haNK™ effector cells (NK cells modified to express both CD16 and a chimeric antigen receptor that binds CD33 on the cell surface) were also found to exhibit cytotoxicity against target PMBC derived MDSCs in vitro. The PMBC derived MDSCs were exposed to CD33CAR/t-haNK™ effector cells at various effector to target (E:T) ratios as shown in FIG. 7. After 4 hours of incubation, CAR-mediated cytotoxicity was determined by flow cytometry. E:T is shown on the X-axis and % of killing of M2 targets is shown on the Y-axis. As demonstrated by this example, CD33-CAR/t-haNK™ cells significantly lysed the MDSCs in comparison to control aNK™ cells.

Example 6

This example demonstrates that THP-1 cells can be differentiated into M2 like macrophages.

Methods: In vitro differentiation of M2 Macrophage from THP-1 (a human monocytic cell line).

Isolation of TAMs from patient tumor samples is very challenging. Therefore, to mimic TAM in vitro, THP-1 cells were differentiated into M2 like macrophages. The THP-1 cells were first activated in presence of 100 nM PMA for 24 hours, followed by incubating them with 100 nM PMA, 20 ng/ml IL-4 and 20 ng/ml of IL-13 for 48 hours. The macrophage-like phenotype was characterized by changes in morphology as observed by light microscopy (FIG. 8A). The photomicrographs show the morphology of THP-1 cells changes when differentiated into M2 cells, which become large and adherent. The M2 macrophages were also characterized by increased cell surface expression of M2 macrophage markers like CD 206 and CD163 by flow cytometry (FIG. 8B). FIG. 8C shows CD33 expression on THP-1 and M2 (differentiated from THP-1 cells). Median fluorescence intensity of CD206 (THP-1=1.82, M2=9.44), CD163 (THP-1=0.37, M2=21.7) and CD33 (THP-1=104, M2=198).

Example 7

Figure 9:
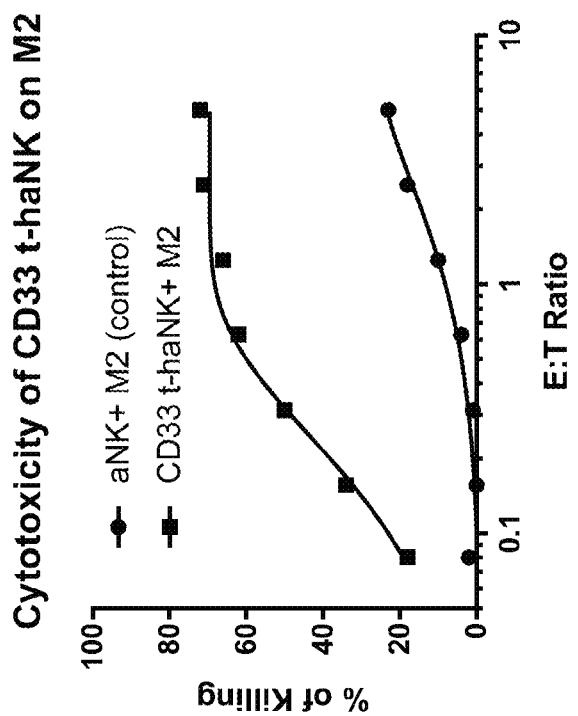
FIG. 9 shows the results of a cytotoxicity assay using CD33 t-haNK™ effector cells against THP-1 derived M2 macrophage target cells. Effector to target cell ratio (E:T) is shown on the X-axis and percent (%) killing of M2 targets is shown on the Y-axis.

This example shows that CD33-CAR/t-haNK™ cells have potential to eliminate M2 macrophages. The THP-1 derived M2 macrophages were exposed to CD33-CAR/t-haNK™ effector cells at various effector to target ratios as shown in FIG. 9. The CD33 t-haNK™ cells were significantly lysed by the M2 macrophage in comparison to control aNK™ cells.

Methods: Cytotoxicity assay of CD33 t-haNK™ on THP-1 derived M2 macrophages. The CD33-CAR/t-haNK™ effector cells were incubated with M2 macrophages target cells at different effector to target ratios (E:T). After 4 hours of incubation, CAR-mediated cytotoxicity was determined by flow cytometry. E:T is shown on the X-axis and % of killing of M2 targets is shown on the Y-axis.

In summary, the data provided above suggests that NK-92® cells that express a CD33-CAR on the cell surface may provide an effective method for treatment of solid tumors by targeting MDSCs and TAMs in the tumor microenvironment.

All publications, patent applications, patent publications, references and Genbank accession numbers cited in the present specification are hereby incorporated by reference.

What is claimed is:

1. A composition comprising a genetically modified T cell or Natural Killer (NK) cell, wherein the modified T cell or NK cell expresses a chimeric antigen receptor (CAR) that specifically targets a tumor-associated antigen, wherein the CAR comprises 1) a first amino acid sequence comprising an antigen binding domain and 2) a second amino acid sequence comprising a CD8 hinge domain, a CD28 transmembrane domain, and an FcεRIγ signaling domain, wherein the second amino acid sequence has at least 95% sequence identity to amino acids 268-401 of SEQ ID NO: 16.

2. The composition of claim 1, wherein the antigen binding domain is an antibody or fragment thereof, a fusion protein comprising heavy and light chain variable regions, or a single chain variable fragment (scFv).

3. The composition of claim 1, wherein the composition is formulated for administration to a subject in need thereof.

4. The composition of claim 1, wherein the genetically modified NK cell further comprises CD16.

5. The composition of claim 4, further comprising an antibody, fragment thereof, or fusion protein comprised thereof, wherein the antibody specifically binds to CD33.

6. The composition of claim 3, wherein administration of the composition results in a reduction of cells expressing the antigen.

7. The composition of claim 5, wherein administration of the composition results in a reduction of cells expressing CD33.

8. The composition of claim 1, further comprising a T cell or an NK cell genetically modified to express a CAR that specifically binds CD33, wherein the CAR comprises an amino acid sequence having at least 95% sequence identity to SEQ ID NO: 16.

9. The composition of claim 3, wherein about 1×10$^8$ to about 1×10$^{11}$ modified cells per m$^2$ of body surface area of the subject are formulated for administration to the subject.

10. The composition of claim 1, wherein the first amino acid sequence is fused to the N-terminus of the second amino acid sequence.

11. The composition of claim 10, wherein the first amino acid sequence is fused to the N-terminus of the second amino acid sequence via a polypeptide linker.

12. A method for reducing the number of myeloid-derived suppressor cells (MDSC), tumor associated macrophages (TAM), or both, in a subject in need thereof, the method comprising: administering to the subject, intravenously or by injection, 1) a therapeutically effective amount of a genetically modified NK cell comprising a) a chimeric antigen receptor (CAR) that specifically binds CD33, wherein the CAR comprises a first amino acid sequence comprising a CD33 binding domain and a second amino acid sequence comprising a CD8 hinge domain, a CD28 transmembrane domain, and an FcεRIγ signaling domain, wherein the second amino acid sequence has at least 95% sequence identity to amino acids 268-401 of SEQ ID NO: 16, and b) a CD16 receptor; and 2) a therapeutically effective amount of an antibody.

13. The method of claim 12, wherein about 1×10$^8$ to about 1×10$^{11}$ modified cells per m$^2$ of body surface area of the subject are administered to the subject.

14. The method of claim 12, wherein the genetically modified NK cells are administered once per 1, 2, 3, or 4 weeks.

15. The method of claim 12, wherein the antibody is specific for a tumor-associated antigen.

16. The method of claim 12, wherein the antibody is specific for CD33.

17. A composition comprising 1) an effective amount of a genetically modified NK cell comprising a) a chimeric antigen receptor (CAR) that specifically binds CD33, wherein the CAR comprises a first amino acid sequence comprising a CD33 binding domain and a second amino acid sequence comprising a CD8 hinge domain, a CD28 transmembrane domain, and an FcεRIγ signaling domain, wherein the second amino acid sequence has at least 95% sequence identity to amino acids 268-401 of SEQ ID NO: 16, and b) a CD16 receptor; and 2) an effective amount of an antibody.

18. The composition of claim 15, wherein about $1\times10^8$ to about $1\times10^{11}$ modified NK cells per $m^2$ of body surface area of the subject are formulated for administration to the subject.

19. The composition of claim 15, wherein the NK cells are genetically engineered to express a cytokine or variant thereof.

20. The composition of claim 17, wherein the cytokine or variant thereof comprises IL-2, IL-12, IL-15, IL-18 and IL-21.

21. The composition of claim 17, wherein the antibody is specific for a tumor-associated antigen.

22. The composition of claim 17, wherein the antibody is specific for CD33.

* * * * *

SEQUENCE LISTING

```
Sequence total quantity: 28
SEQ ID NO: 1                  moltype = AA  length = 41
FEATURE                       Location/Qualifiers
REGION                        1..41
                              note = source = /note="Description of Artificial Sequence:
                              Syntheticpolypeptide"
source                        1..41
                              mol_type = protein
                              organism = synthetic construct
SEQUENCE: 1
LKIQVRKAAI TSYEKSDGVY TGLSTRNQET YETLKHEKPP Q                           41

SEQ ID NO: 2                  moltype = AA  length = 65
FEATURE                       Location/Qualifiers
REGION                        1..65
                              note = source = /note="Description of Artificial Sequence:
                              Syntheticpolypeptide"
source                        1..65
                              mol_type = protein
                              organism = synthetic construct
SEQUENCE: 2
ALSNSIMYFS HFVPVFLPAK PTTTPAPRPP TPAPTIASQP LSLRPEACRP AAGGAVHTRG       60
LDFAC                                                                  65

SEQ ID NO: 3                  moltype = AA  length = 28
FEATURE                       Location/Qualifiers
REGION                        1..28
                              note = source = /note="Description of Artificial Sequence:
                              Syntheticpeptide"
source                        1..28
                              mol_type = protein
                              organism = synthetic construct
SEQUENCE: 3
FWVLVVVGGV LACYSLLVTV AFIIFWVR                                          28

SEQ ID NO: 4                  moltype = AA  length = 41
FEATURE                       Location/Qualifiers
REGION                        1..41
                              note = source = /note="Description of Artificial Sequence:
                              Syntheticpolypeptide"
source                        1..41
                              mol_type = protein
                              organism = synthetic construct
SEQUENCE: 4
RSKRSRLLHS DYMNMTPRRP GPTRKHYQPY APPRDFAAYR S                           41

SEQ ID NO: 5                  moltype = AA  length = 42
FEATURE                       Location/Qualifiers
REGION                        1..42
                              note = source = /note="Description of Artificial Sequence:
                              Syntheticpolypeptide"
source                        1..42
                              mol_type = protein
                              organism = synthetic construct
SEQUENCE: 5
KRGRKKLLYI FKQPFMRPVQ TTQEEDGCSC RFPEEEEGGC EL                          42

SEQ ID NO: 6                  moltype = AA  length = 113
FEATURE                       Location/Qualifiers
REGION                        1..113
                              note = source = /note="Description of Artificial Sequence:
                              Syntheticpolypeptide"
source                        1..113
                              mol_type = protein
                              organism = synthetic construct
SEQUENCE: 6
RVKFSRSADA PAYQQGQNQL YNELNLGRRE EYDVLDKRRG RDPEMGGKPQ RRKNPQEGLY       60
NELQKDKMAE AYSEIGMKGE RRRGKGHDGL YQGLSTATKD TYDALHMQAL PPR              113

SEQ ID NO: 7                  moltype = AA  length = 153
FEATURE                       Location/Qualifiers
source                        1..153
                              mol_type = protein
                              organism = Homo sapiens
SEQUENCE: 7
MYRMQLLSCI ALSLALVTNS APTSSSTKKT QLQLEHLLLD LQMILNGINN YKNPKLTRML       60
TFKFYMPKKA TELKHLQCLE EELKPLEEVL NLAQSKNFHL RPRDLISNIN VIVLELKGSE       120
TTFMCEYADE TATIVEFLNR WITFCQSIIS TLT                                    153
```

```
SEQ ID NO: 8              moltype = AA   length = 160
FEATURE                   Location/Qualifiers
REGION                    1..160
                          note = source = /note="Description of Artificial Sequence:
                          Syntheticpolypeptide"
source                    1..160
                          mol_type = protein
                          organism = synthetic construct
SEQUENCE: 8
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLTGSEKDEL                         160

SEQ ID NO: 9              moltype = AA   length = 236
FEATURE                   Location/Qualifiers
source                    1..236
                          mol_type = protein
                          organism = Homo sapiens
SEQUENCE: 9
RTEDLPKAVV FLEPQWYRVL EKDSVTLKCQ GAYSPEDNST QWFHNESLIS SQASSYFIDA    60
ATVDDSGEYR CQTNLSTLSD PVQLEVHIGW LLLQAPRIHLRC HSWKNTALHK           120
VTYLQNGKGR KYFHHNSDFY IPKATLKDSG SYFCRGLFGS KNVSSETVNI TITQGLAVST   180
ISSFFPPGYQ VSFCLVMVLL FAVDTGLYFS VKTNIRSSTR DWKDHKFKWR KDPQDK       236

SEQ ID NO: 10             moltype = AA   length = 236
FEATURE                   Location/Qualifiers
source                    1..236
                          mol_type = protein
                          organism = Homo sapiens
SEQUENCE: 10
RTEDLPKAVV FLEPQWYRVL EKDSVTLKCQ GAYSPEDNST QWFHNESLIS SQASSYFIDA    60
ATVDDSGEYR CQTNLSTLSD PVQLEVHIGW LLLQAPRWVF KEEDPIHLRC HSWKNTALHK   120
VTYLQNGKGR KYFHHNSDFY IPKATLKDSG SYFCRGLVGS KNVSSETVNI TITQGLAVST   180
ISSFFPPGYQ VSFCLVMVLL FAVDTGLYFS VKTNIRSSTR DWKDHKFKWR KDPQDK       236

SEQ ID NO: 11             moltype = AA   length = 254
FEATURE                   Location/Qualifiers
source                    1..254
                          mol_type = protein
                          organism = Homo sapiens
SEQUENCE: 11
MWQLLLPTAL LLLVSAGMRT EDLPKAVVFL EPQWYRVLEK DSVTLKCQGA YSPEDNSTQW    60
FHNESLISSQ ASSYFIDAAT VDDSGEYRCQ TNLSTLSDPV QLEVHIGWLL LQAPRWVFKE   120
EDPIHLRCHS WKNTALHKVT YLQNGKGRKY FHHNSDFYIP KATLKDSGSY FCRGLFGSKN   180
VSSETVNITI TQGLAVSTIS SFFPPGYQVS FCLVMVLLFA VDTGLYFSVK TNIRSSTRDW   240
KDHKFKWRKD PQDK                                                     254

SEQ ID NO: 12             moltype = AA   length = 254
FEATURE                   Location/Qualifiers
source                    1..254
                          mol_type = protein
                          organism = Homo sapiens
SEQUENCE: 12
MWQLLLPTAL LLLVSAGMRT EDLPKAVVFL EPQWYRVLEK DSVTLKCQGA YSPEDNSTQW    60
FHNESLISSQ ASSYFIDAAT VDDSGEYRCQ TNLSTLSDPV QLEVHIGWLL LQAPRWVFKE   120
EDPIHLRCHS WKNTALHKVT YLQNGKGRKY FHHNSDFYIP KATLKDSGSY FCRGLVGSKN   180
VSSETVNITI TQGLAVSTIS SFFPPGYQVS FCLVMVLLFA VDTGLYFSVK TNIRSSTRDW   240
KDHKFKWRKD PQDK                                                     254

SEQ ID NO: 13             moltype = DNA  length = 765
FEATURE                   Location/Qualifiers
source                    1..765
                          mol_type = unassigned DNA
                          organism = Homo sapiens
SEQUENCE: 13
atgtggcagc tgctcctccc aactgctctg ctacttctag tttcagctgg catgcggact    60
gaagatctcc caaggctgt ggtgttcctg gagcctcaat ggtacagggt gctcgagaag   120
gacagtgtga ctctgaagtg ccagggagcc tactccccta aggacaattc cacacagtgg   180
tttcacaatg agagcctcat ctcaagccag gcctcgagct acttcattga cgctgccaca   240
gtcgacgaca gtggagagta caggtgccag acaaacctct ccaccctcag tgacccggtg   300
cagctagaag tccatatcgg ctggctgttg ctccaggccc ctcggtgggt gttcaaggag   360
gaagacccta ttcacctgag gtgtcacagc tggaagaaca ctgctctgca taaggtcaca   420
tatttacaga atggcaaagg caggaagtat tttcatcata attctgactt ctacattcca   480
aaagccacac tcaaagacag cggctcctac ttctgcaggg gcttttttgg gagtaaaaat   540
gtgtcttcag agactgtgaa catcaccatc actcaaggtt tggcagtgtc aaccatctca   600
tcattctttc cacctgggta ccaagtgtct ttctgcttgg tgatggtact ccttttttgca   660
gtggacacag gactatattt ctctgtgaag acaaacattc gaagctcaac aagagactgg   720
aaggaccata aatttaaatg gagaaaggac cctcaagaca atga                    765
```

```
SEQ ID NO: 14           moltype = DNA  length = 795
FEATURE                 Location/Qualifiers
misc_feature            1..795
                        note = source = /note="Description of Artificial Sequence:
                        Syntheticpolynucleotide"
source                  1..795
                        mol_type = other DNA
                        organism = synthetic construct
SEQUENCE: 14
atggactgga tctggcgcat cctcttcctc gtcggcgctg ctaccggcgc tcattcggcc    60
cagccggccg acattcaaat gactcagtcc ccttccagct tgtcagcctc agtaggggac   120
cgggtcacga tcacctgtcg agcgtctgag tcagtggata actacgggat ttctttcatg   180
aactggttcc agcagaagcc cggcaaagct cctaagctcc ttatatatgc agcctcaaat   240
caggggagcg gtgttcctag tcgcttcagt ggaagcggta gcggtacgga ctttacgttg   300
acgataagta gccttcagcc agatgacttt gccacttatt attgtcagca gtctaaggaa   360
gttccttgga cgtttggcca aggaacgaag gtcgaaatca aggggggagg gggctcagga   420
gggggcggca gtggtggtgg aggctctcaa gtccaactcg tacagtctgg cgcggaggtt   480
aaaaagccgg gaagctccgt gaaagtatcc tgtaaggcaa gcggatacac ctttaccgat   540
tataacatgc actgggttag gcaggcgccc ggccaaggtc tggaatggat cggttatatt   600
tatccataca acggtggtac cggctataat cagaagttta agagtaaggc tactattaca   660
gcggatgagt caaccaatac tgcatacatg gagctctcct cactcaggag cgaagatacc   720
gcagtgtatt actgtgcccg agggagacca gccatggact actgggggtca gggtacccct  780
gtgacagtat ctagc                                                   795

SEQ ID NO: 15           moltype = AA  length = 265
FEATURE                 Location/Qualifiers
REGION                  1..265
                        note = source = /note="Description of Artificial Sequence:
                        Syntheticpolypeptide"
source                  1..265
                        mol_type = protein
                        organism = synthetic construct
SEQUENCE: 15
MDWIWRILFL VGAATGAHSA QPADIQMTQS PSSLSASVGD RVTITCRASE SVDNYGISFM    60
NWFQQKPGKA PKLLIYAASN QGSGVPSRFS GSGSGTDFTL TISSLQPDDF ATYYCQQSKE   120
VPWTFGQGTK VEIKGGGSG GGGSGGGGSQ VQLVQSGAEV KKPGSSVKVS CKASGYTFTD   180
YNMHWVRQAP GQGLEWIGYI YPYNGGTGYN QKFKSKATIT ADESTNTAYM ELSSLRSEDT   240
AVYYCARGRP AMDYWGQGTL VTVSS                                        265

SEQ ID NO: 16           moltype = AA  length = 401
FEATURE                 Location/Qualifiers
REGION                  1..401
                        note = source = /note="Description of Artificial Sequence:
                        Syntheticpolypeptide"
source                  1..401
                        mol_type = protein
                        organism = synthetic construct
SEQUENCE: 16
MDWIWRILFL VGAATGAHSA QPADIQMTQS PSSLSASVGD RVTITCRASE SVDNYGISFM    60
NWFQQKPGKA PKLLIYAASN QGSGVPSRFS GSGSGTDFTL TISSLQPDDF ATYYCQQSKE   120
VPWTFGQGTK VEIKGGGSG GGGSGGGGSQ VQLVQSGAEV KKPGSSVKVS CKASGYTFTD   180
YNMHWVRQAP GQGLEWIGYI YPYNGGTGYN QKFKSKATIT ADESTNTAYM ELSSLRSEDT   240
AVYYCARGRP AMDYWGQGTL VTVSSAAALS NSIMYFSHFV PVFLPAKPTT TPAPRPPTPA   300
PTIASQPLSL RPEACRPAAG GAVHTRGLDF ACFWVLVVVG GVLACYSLLV TVAFIIFWVR   360
LKIQVRKAAI TSYEKSDGVY TGLSTRNQET YETLKHEKPP Q                      401

SEQ ID NO: 17           moltype = DNA  length = 1203
FEATURE                 Location/Qualifiers
misc_feature            1..1203
                        note = source = /note="Description of Artificial Sequence:
                        Syntheticpolynucleotide"
source                  1..1203
                        mol_type = other DNA
                        organism = synthetic construct
SEQUENCE: 17
atggactgga tctggcgcat cctcttcctc gtcggcgctg ctaccggcgc tcattcggcc    60
cagccggccg acattcaaat gactcagtcc ccttccagct tgtcagcctc agtaggggac   120
cgggtcacga tcacctgtcg agcgtctgag tcagtggata actacgggat ttctttcatg   180
aactggttcc agcagaagcc cggcaaagct cctaagctcc ttatatatgc agcctcaaat   240
caggggagcg gtgttcctag tcgcttcagt ggaagcggta gcggtacgga ctttacgttg   300
acgataagta gccttcagcc agatgacttt gccacttatt attgtcagca gtctaaggaa   360
gttccttgga cgtttggcca aggaacgaag gtcgaaatca aggggggagg gggctcagga   420
gggggcggca gtggtggtgg aggctctcaa gtccaactcg tacagtctgg cgcggaggtt   480
aaaaagccgg gaagctccgt gaaagtatcc tgtaaggcaa gcggatacac ctttaccgat   540
tataacatgc actgggttag gcaggcgccc ggccaaggtc tggaatggat cggttatatt   600
tatccataca acggtggtac cggctataat cagaagttta agagtaaggc tactattaca   660
gcggatgagt caaccaatac tgcatacatg gagctctcct cactcaggag cgaagatacc   720
gcagtgtatt actgtgcccg agggagacca gccatggact actgggggtca gggtacccct  780
```

```
gtgacagtat ctagcgcggc cgcgctgagc aacagcatca tgtacttcag ccacttcgtg    840
cctgtgttcc tgcctgccaa gcctacaaca caccagccc  ctagacctcc aacccctgcc    900
cctacaattg cctctcagcc tctgtctctg aggcccgaag cttgtagacc tgctgctggc    960
ggagctgtgc acaccagagg actggatttc gcctgctttt gggtgctggt ggtcgtgggc   1020
ggagtgctgg cttgttattc tctgctggtc accgtgctgt tcatcatctt ttgggtccga   1080
ctgaagatcc aggtccgaaa ggccgccatc accagctacg agaagtctga tggcgtgtac   1140
accggcctga gcaccagaaa ccaggaaacc tacgagacac tgaagcacga gaagcccccc   1200
cag                                                                 1203
```

| | | |
|---|---|---|
| SEQ ID NO: 18 | moltype = AA length = 15 | |
| FEATURE | Location/Qualifiers | |
| REGION | 1..15 | |
| | note = source = /note="Description of Artificial Sequence: Syntheticpeptide" | |
| source | 1..15 | |
| | mol_type = protein | |
| | organism = synthetic construct | |
| SEQUENCE: 18 | | |
| RASESVDNYG ISFMN | | 15 |

| | | |
|---|---|---|
| SEQ ID NO: 19 | moltype = AA length = 6 | |
| FEATURE | Location/Qualifiers | |
| REGION | 1..6 | |
| | note = source = /note="Description of Artificial Sequence: Syntheticpeptide" | |
| source | 1..6 | |
| | mol_type = protein | |
| | organism = synthetic construct | |
| SEQUENCE: 19 | | |
| ASNQGS | | 6 |

| | | |
|---|---|---|
| SEQ ID NO: 20 | moltype = AA length = 9 | |
| FEATURE | Location/Qualifiers | |
| REGION | 1..9 | |
| | note = source = /note="Description of Artificial Sequence: Syntheticpeptide" | |
| source | 1..9 | |
| | mol_type = protein | |
| | organism = synthetic construct | |
| SEQUENCE: 20 | | |
| QQSKEVPWT | | 9 |

| | | |
|---|---|---|
| SEQ ID NO: 21 | moltype = AA length = 5 | |
| FEATURE | Location/Qualifiers | |
| REGION | 1..5 | |
| | note = source = /note="Description of Artificial Sequence: Syntheticpeptide" | |
| source | 1..5 | |
| | mol_type = protein | |
| | organism = synthetic construct | |
| SEQUENCE: 21 | | |
| DYNMH | | 5 |

| | | |
|---|---|---|
| SEQ ID NO: 22 | moltype = AA length = 17 | |
| FEATURE | Location/Qualifiers | |
| REGION | 1..17 | |
| | note = source = /note="Description of Artificial Sequence: Syntheticpeptide" | |
| source | 1..17 | |
| | mol_type = protein | |
| | organism = synthetic construct | |
| SEQUENCE: 22 | | |
| YIYPYNGGTG YNQKFKS | | 17 |

| | | |
|---|---|---|
| SEQ ID NO: 23 | moltype = AA length = 7 | |
| FEATURE | Location/Qualifiers | |
| REGION | 1..7 | |
| | note = source = /note="Description of Artificial Sequence: Syntheticpeptide" | |
| source | 1..7 | |
| | mol_type = protein | |
| | organism = synthetic construct | |
| SEQUENCE: 23 | | |
| GRPAMDY | | 7 |

| | | |
|---|---|---|
| SEQ ID NO: 24 | moltype = AA length = 111 | |
| FEATURE | Location/Qualifiers | |
| REGION | 1..111 | |
| | note = source = /note="Description of Artificial Sequence: | |

```
                        Syntheticpolypeptide"
source                  1..111
                        mol_type = protein
                        organism = synthetic construct
SEQUENCE: 24
DIQMTQSPSS LSASVGDRVT ITCRASESVD NYGISFMNWF QQKPGKAPKL LIYAASNQGS     60
GVPSRFSGSG SGTDFTLTIS SLQPDDFATY YCQQSKEVPW TFGQGTKVEI K             111

SEQ ID NO: 25           moltype = AA   length = 116
FEATURE                 Location/Qualifiers
REGION                  1..116
                        note = source = /note="Description of Artificial Sequence:
                        Syntheticpolypeptide"
source                  1..116
                        mol_type = protein
                        organism = synthetic construct
SEQUENCE: 25
QVQLVQSGAE VKKPGSSVKV SCKASGYTFT DYNMHWVRQA PGQGLEWIGY IYPYNGGTGY     60
NQKFKSKATI TADESTNTAY MELSSLRSED TAVYYCARGR PAMDYWGQGT LVTVSS        116

SEQ ID NO: 26           moltype = AA   length = 4
FEATURE                 Location/Qualifiers
REGION                  1..4
                        note = source = /note="Description of Unknown:'KDEL' motif
                        peptide"
source                  1..4
                        mol_type = protein
                        organism = unidentified
SEQUENCE: 26
KDEL                                                                   4

SEQ ID NO: 27           moltype = DNA   length = 3126
FEATURE                 Location/Qualifiers
misc_feature            1..3126
                        note = source = /note="Description of Artificial Sequence:
                        Syntheticpolynucleotide"
source                  1..3126
                        mol_type = other DNA
                        organism = synthetic construct
SEQUENCE: 27
atggactgga tctggcgcat cctcttcctc gtcggcgctg ctaccggcgc tcattcggcc     60
cagccggccg acattcaaat gactcagtcc ccttccagct gtcagcctc agtagggac     120
cgggtcacga tcacctgtcg agcgtctgag tcagtggata actacgggat ttctttcatg    180
aactggttcc agcagaagcc cggcaaagct cctaagctcc ttatatatgc agcctcaaat    240
caggggagcg tgttcctag tcgcttcagt ggaagcggta gcggtacgga cttttacgttg    300
acgataagta gccttcagcc agatgacttt gccacttatt attgtcagca gtctaaggaa    360
gttccttgga cgtttggcca aggaacgaag gtcgaaatca aaggggagg gggctcagga    420
ggggggcggca gtggtggtgg aggctctcaa gtccaactcg tacagtctgg cgcggaggtt    480
aaaaagccgg gaagctccgt gaaagtatcc tgtaaggcaa gcggatacac ctttaccgat    540
tataacatgc actgggttag gcaggcgccc ggccaaggtc tggaatggat cggttatatt    600
tatccataca acggtggtac cggctataat cagaagtta agagtaaggc tactattaca    660
gcggatgagt caaccaatac tgcatacatg gagctctcct cactcaggag cgaagatacc    720
gcagtgtatt actgtgcccg agggagacca gccatggact actggggtca gggtacctt    780
gtgacagtat ctagcgcggc cgcgctgagc aacagcatca tgtacttcag ccacttcgtg    840
cctgtgttcc tgcctgccaa gcctacaaca caccagcctc ctagacctcc aacccctgcg    900
cctacaattg cctctcagcc tctgtctctg aggcccgaag cttgtagacc tgctgctggc    960
ggagctgtgc acaccagagg actggatttc gcctgctttt gggtgctggt ggtcgtggggc  1020
ggagtgctgg cttgttattc tctgctggtc accgtggcct tcatcatctt ttgggtccga   1080
ctgaagatcc aggtccgaaa ggccgccatc accagctacg agaagtctga tggcgtgtac   1140
accggcctga gcaccagaaa ccaggaaacc tacgagacac tgaagacgga gaagcccc    1200
cagggatccg gagctactaa cttcagcctg ctgaagcagg ctggagacgt ggaggagaac   1260
cctgaccta tgtggcagct gctgctgcct acagctctcc tgctgctggt gtccgccggc   1320
atgagaaccg aggatctgcc taaggccgtg gtgttcctgg aacccagtg gtacagagtg   1380
ctggaaaagg acagcgtgac cctgaagtgc caggggcct caggcccccga ggacaatagc   1440
acccagtggt tccacaacga gagcctgatc agcagccagg ccagcagcta cttcatcgac   1500
gccgccaccg tggacgacag cggcgagtat agatgccaga ccaacctgag caccctgagc   1560
gaccccgtgc agctggaagt gcacatcgga tggctgctgc tgcaggcccc cagatggtgt   1620
ttcaaagaag aggaccccat ccacctgaga tgccactctt ggaagaacac cgccctgcac   1680
aaagtgacct acctgcagaa cggcaaggac agaaagtact tccaccacaa cagcgacttc   1740
tacatcccca aggccaccct gaaggactcc ggctcctact tctgcagagg cctcgtgggc   1800
agcaagaacg tgtccagcga gacagtgaac atcaccatca cccaggggct ggccgtgtct   1860
accatcagca gcttttttccc accggctac caggtgtcct tctgcctcgt gatggtgctg   1920
ctgttcgccg tggacaccgg cctgtacttc agcgtgaaaa caaacatcag aagcagcacc   1980
cgggactgga aggaccacaa gttcaagtgg cggaaggacc cccaggacaa gtgaattcc   2040
gcccctctcc ccccccccc tctccctccc cccccctaa cgttactggc cgaagccgct   2100
tggaataagg ccggtgtgcg tttgtctata tgttattttc caccatattg ccgtcttttg   2160
gcaatgtgag ggcccggaaa cctggccctg tcttcttgac gagcattcct aggggtcttt   2220
cccctctcgc caaaggaatg caaggtctgt tgaatgtcgt gaaggaagca gttcctctgg   2280
aagcttcttg aagacaaaca acgtctgtag cgacccttg caggcagcgg aacccccac    2340
```

-continued

```
ctggcgacag gtgcctctgc ggccaaaagc cacgtgtata agatacacct gcaaaggcgg  2400
cacaacccca gtgccacgtt gtgagttgga tagttgtgga aagagtcaaa tggctctcct  2460
caagcgtatt caacaagggg ctgaaggatg cccagaaggt accccattgt atgggatctg  2520
atctggggcc tcgtgcaca tgctttacat gtgtttagtc gaggttaaaa aaacgtctag  2580
gcccccgaa ccacgggac gtggttttcc tttgaaaaac acgataaccg ccaccatgta  2640
ccggatgcag ctgctgagct gtatcgccct gtctctggcc ctcgtgacca acagcgcccc  2700
taccagcagc agcaccaaga aaacccagct gcagctggaa catctgctgc tggacctgca  2760
gatgatcctg aacggcatca acaactacaa gaacccaag ctgacccgga tgctgacctt  2820
caagttctac atgcccaaga aggccaccga actgaaacat ctgcagtgcc tggaagagga  2880
actgaagccc ctggaagaag tgctgaacct ggcccagagc aagaacttcc acctgaggcc  2940
cagggacctg atcagcaaca tcaacgtgat cgtgctggaa ctgaaaggca gcagacaac  3000
cttcatgtgc gagtacgccg acgagacagc taccatcgtg gaatttctga accggtggat  3060
caccttctgc cagagcatca tcagcaccct gaccggctcc gagaaggacg agctgtgagc  3120
ggccgc                                                             3126

SEQ ID NO: 28          moltype = AA  length = 677
FEATURE                Location/Qualifiers
REGION                 1..677
                       note = source = /note="Description of Artificial Sequence:
                       Syntheticpolypeptide"
source                 1..677
                       mol_type = protein
                       organism = synthetic construct
SEQUENCE: 28
MDWIWRILFL VGAATGAHSA QPADIQMTQS PSSLSASVGD RVTITCRASE SVDNYGISFM   60
NWFQQKPGKA PKLLIYAASN QGSGVPSRFS GSGSGTDFTL TISSLQPDDF ATYYCQQSKE  120
VPWTFGQGTK VEIKGGGSSG GGGSGGGGSQ VQLVQSGAEV KKPGSSVKVS CKASGYTFTD  180
YNMHWVRQAP GQGLEWIGYI YPYNGGTGYN QKFKSKATIT ADESTNTAYM ELSSLRSEDT  240
AVYYCARGRP AMDYWGQGTL VTVSSAAALS NSIMYFSHFV PVFLPAKPTT TPAPRPPTPA  300
PTIASQPLSL RPEACRPAAG GAVHTRGLDF ACFWVLVVVG GVLACYSLLV TVAFIIFWVR  360
LKIQVRKAAI TSYEKSDGVY TGLSTRNQET YETLKHEKPP QGSGATNFSL LKQAGDVEEN  420
PGPMWQLLLP TALLLLVSAG MRTEDLPKAV VFLEPQWYRV LEKDSVTLKC QGAYSPEDNS  480
TQWFHNESLI SSQASSYFID AATVDDSGEY RCQTNLSTLS DPVQLEVHIG WLLLQAPRWV  540
FKEEDPIHLR CHSWKNTALH KVTYLQNGKG RKYFHHNSDF YIPKATLKDS GSYFCRGLVG  600
SKNVSSETVN ITITQGLAVS TISSFFPPGY QVSFCLVMVL LFAVDTGLYF SVKTNIRSST  660
RDWKDHKFKW RKDPQDK                                                 677
```